US009248306B2

(12) United States Patent
Joo et al.

(10) Patent No.: US 9,248,306 B2
(45) Date of Patent: Feb. 2, 2016

(54) PULSE DETECTION APPARATUS, SOFTWARE, AND METHODS USING PATIENT PHYSIOLOGICAL SIGNALS

(71) Applicant: Physio-Control, Inc., Redmond, WA (US)

(72) Inventors: Tae H. Joo, Redmond, WA (US); Ronald E. Stickney, Edmonds, WA (US); Cynthia P. Jayne, Redmond, WA (US); Paula Lank, Renton, WA (US); Patricia O'Hearn, Mercer Island, WA (US); David R. Hampton, Woodinville, WA (US); James W. Taylor, Sammamish, WA (US); William E. Crone, Fall City, WA (US); Daniel Yerkovich, Seattle, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 0 days.

(21) Appl. No.: 13/970,522

(22) Filed: Aug. 19, 2013

(65) Prior Publication Data

US 2013/0338724 A1 Dec. 19, 2013

Related U.S. Application Data

(60) Continuation-in-part of application No. 13/267,783, filed on Oct. 6, 2011, now Pat. No. 8,532,766, which is a continuation of application No. 13/032,250, filed on Feb. 22, 2011, now Pat. No. 8,239,024, which is a

(51) Int. Cl.
*A61N 1/39* (2006.01)
*A61M 16/00* (2006.01)
(Continued)

(52) U.S. Cl.
CPC ............ *A61N 1/3987* (2013.01); *A61B 5/0535* (2013.01); *A61B 7/00* (2013.01);
(Continued)

(58) Field of Classification Search
CPC ... A61N 1/3993; A61N 1/39; A61M 16/0051; A61M 16/0048
USPC .................................................. 607/4–6, 18
See application file for complete search history.

(56) References Cited

U.S. PATENT DOCUMENTS 3,318,303 A 5/1967 Hammacher
3,716,059 A 2/1973 Welborn et al.
(Continued)

FOREIGN PATENT DOCUMENTS

EP 0339471 A2 11/1989
EP 0435500 A1 7/1991
(Continued)

OTHER PUBLICATIONS

"American Heart Guidelines 2000 for Cardiopulmonary Resuscitation and Emergency Cardiovascular Care, Part 3: Adult Basic Life Support," Circulation 102 Suppl. I:I-22 to I-59, 2000.
(Continued)

*Primary Examiner* — George Evanisko
(74) *Attorney, Agent, or Firm* — Marger Johnson

(57) ABSTRACT

A cardiac pulse in a patient is determined by evaluating physiological signals in the patient. A medical device evaluates two or more different physiological signals, such as phonocardiogram (PCG) signals, electrocardiogram (ECG) signals, patient impedance signals, piezoelectric signals, and accelerometer signals for features indicative of the presence of a cardiac pulse. Using these features, the medical device determines whether a cardiac pulse is present in the patient. The medical device may also be configured to report whether the patient is in a VF, VT, asystole, or PEA condition, in addition to being in a pulseless condition, and prompt different therapies, such as chest compressions, rescue breathing, defibrillation, and PEA-specific electrotherapy, depending on the analysis of the physiological signals. Auto-capture of a cardiac pulse using pacing stimuli is further provided. The medical devices, or any portion thereof, can be worn by the patient or may be attached to the patient.

19 Claims, 20 Drawing Sheets

Related U.S. Application Data division of application No. 11/167,247, filed on Jun. 27, 2005, now Pat. No. 7,917,209, which is a division of application No. 10/229,320, filed on Aug. 26, 2002, now abandoned, which is a continuation-in-part of application No. 09/410,198, filed on Sep. 3, 1999, now Pat. No. 6,440,082, and a continuation-in-part of application No. 10/013,941, filed on Dec. 6, 2001, now abandoned.

(51) Int. Cl.
*A61B 7/00* (2006.01)
*A61B 7/04* (2006.01)
*A61B 5/053* (2006.01)
*A61B 5/00* (2006.01)
*A61B 5/0464* (2006.01)
*A61B 5/08* (2006.01)
*A61N 1/365* (2006.01)

(52) U.S. Cl.
CPC .............. *A61B 7/04* (2013.01); *A61M 16/00* (2013.01); *A61N 1/39* (2013.01); *A61N 1/3925* (2013.01); *A61B 5/0464* (2013.01); *A61B 5/0809* (2013.01); *A61B 5/7264* (2013.01); *A61N 1/36578* (2013.01)

(56) References Cited

U.S. PATENT DOCUMENTS

| | | |
|---|---|---|
| 3,805,795 A | 4/1974 | Denniston et al. |
| 3,871,359 A | 3/1975 | Pacela |
| 4,102,332 A | 7/1978 | Gessman |
| RE30,101 E | 9/1979 | Kubicek et al. |
| 4,181,134 A | 1/1980 | Mason et al. |
| 4,220,160 A | 9/1980 | Kimball et al. |
| RE30,750 E | 9/1981 | Diack et al. |
| 4,291,699 A | 9/1981 | Geddes et al. |
| 4,428,380 A | 1/1984 | Wong et al. |
| 4,446,873 A | 5/1984 | Groch et al. |
| 4,450,527 A | 5/1984 | Sramek |
| 4,519,397 A | 5/1985 | Tabata |
| 4,548,204 A | 10/1985 | Groch et al. |
| 4,559,946 A | 12/1985 | Mower |
| 4,562,843 A | 1/1986 | Djordjevich et al. |
| 4,610,254 A | 9/1986 | Morgan et al. |
| 4,777,962 A | 10/1988 | Watson et al. |
| 4,792,145 A | 12/1988 | Eisenberg et al. |
| 4,896,675 A | 1/1990 | Ohsuga et al. |
| 4,919,145 A | 4/1990 | Marriott |
| 4,928,674 A | 5/1990 | Halperin et al. |
| 4,928,690 A | 5/1990 | Heilman et al. |
| 4,947,859 A | 8/1990 | Brewer et al. |
| 4,951,679 A | 8/1990 | Harada |
| 4,955,381 A | 9/1990 | Way et al. |
| 4,967,760 A | 11/1990 | Bennett, Jr. et al. |
| 5,002,052 A | 3/1991 | Haluska |
| 5,035,247 A | 7/1991 | Heimann |
| 5,036,857 A | 8/1991 | Semmlow et al. |
| 5,077,667 A | 12/1991 | Brown et al. |
| 5,078,134 A | 1/1992 | Heilman et al. |
| 5,178,154 A | 1/1993 | Ackmann et al. |
| 5,184,620 A | 2/1993 | Cudahy et al. |
| 5,243,975 A | 9/1993 | Alferness et al. |
| 5,261,418 A | 11/1993 | Ferek-Petric |
| 5,273,036 A | 12/1993 | Kronberg et al. |
| 5,305,745 A | 4/1994 | Zacouto |
| 5,318,592 A | 6/1994 | Schaldach |
| 5,330,506 A | 7/1994 | Alferness et al. |
| 5,337,752 A | 8/1994 | Reeves |
| 5,339,819 A | 8/1994 | Takashima |
| 5,353,793 A | 10/1994 | Bornn |
| 5,362,966 A | 11/1994 | Rosenthal et al. |
| 5,366,486 A | 11/1994 | Zipes et al. |
| 5,392,780 A | 2/1995 | Ogino et al. |
| 5,404,877 A | 4/1995 | Nolan et al. |
| 5,405,362 A | 4/1995 | Kramer et al. |
| 5,423,326 A | 6/1995 | Wang et al. |
| 5,425,750 A | 6/1995 | Moberg |
| 5,431,688 A | 7/1995 | Freeman |
| 5,433,731 A | 7/1995 | Hoegnelid et al. |
| 5,443,072 A | 8/1995 | Kagan et al. |
| 5,458,621 A | 10/1995 | White et al. |
| RE35,122 E | 12/1995 | Corenman et al. |
| 5,474,574 A | 12/1995 | Payne et al. |
| 5,490,516 A | 2/1996 | Hutson |
| 5,497,779 A | 3/1996 | Takaya et al. |
| 5,617,868 A | 4/1997 | Harada et al. |
| 5,620,003 A | 4/1997 | Sepponen |
| 5,622,182 A | 4/1997 | Jaffe |
| 5,683,424 A | 11/1997 | Brown et al. |
| 5,685,317 A | 11/1997 | Sjostrom |
| 5,687,738 A | 11/1997 | Shapiro et al. |
| 5,700,283 A | 12/1997 | Salo |
| 5,702,427 A | 12/1997 | Ecker et al. |
| 5,704,363 A | 1/1998 | Amano |
| 5,727,561 A | 3/1998 | Owsley |
| 5,776,071 A | 7/1998 | Inukai et al. |
| 5,795,300 A | 8/1998 | Bryars |
| 5,807,268 A | 9/1998 | Reeves et al. |
| 5,825,895 A | 10/1998 | Grasfield et al. |
| 5,885,222 A | 3/1999 | Kassal et al. |
| 6,005,658 A | 12/1999 | Kaluza et al. |
| 6,050,950 A | 4/2000 | Mohler |
| 6,053,872 A | 4/2000 | Mohler |
| 6,104,953 A | 8/2000 | Leyde |
| 6,122,536 A | 9/2000 | Sun et al. |
| 6,125,298 A | 9/2000 | Olson et al. |
| 6,125,299 A | 9/2000 | Groenke et al. |
| 6,141,584 A | 10/2000 | Rockwell et al. |
| 6,149,670 A | 11/2000 | Worthen et al. |
| 6,155,257 A | 12/2000 | Lurie et al. |
| 6,161,038 A | 12/2000 | Schookin et al. |
| 6,171,256 B1 | 1/2001 | Joo et al. |
| 6,179,783 B1 | 1/2001 | Mohler |
| 6,208,897 B1 | 3/2001 | Jorgenson et al. |
| 6,293,915 B1 | 9/2001 | Amano et al. |
| 6,298,267 B1 | 10/2001 | Rosborough et al. |
| 6,304,773 B1 | 10/2001 | Taylor et al. |
| 6,304,780 B1 | 10/2001 | Owen et al. |
| 6,312,399 B1 | 11/2001 | Lurie et al. |
| 6,356,785 B1 | 3/2002 | Snyder et al. |
| 6,371,920 B1 | 4/2002 | Kamimoto et al. |
| 6,393,320 B2 | 5/2002 | Lasersohn et al. |
| 6,405,080 B1 | 6/2002 | Lasersohn et al. |
| 6,428,483 B1 | 8/2002 | Carlebach |
| 6,440,082 B1 | 8/2002 | Joo et al. |
| 6,443,906 B1 | 9/2002 | Ting et al. |
| 6,501,983 B1 | 12/2002 | Natarajan et al. |
| 6,516,224 B2 | 2/2003 | Lasersohn et al. |
| 6,575,914 B2 | 6/2003 | Rock et al. |
| 6,587,723 B1 | 7/2003 | Sloman et al. |
| 6,589,271 B1 | 7/2003 | Tzeng et al. |
| 6,650,940 B1 | 11/2003 | Zhu et al. |
| 6,682,551 B1 | 1/2004 | Worthen et al. |
| 6,726,710 B2 | 4/2004 | Worthen et al. |
| 7,011,637 B2 | 3/2006 | Sherman et al. |
| 7,118,542 B2 | 10/2006 | Palazzolo et al. |
| 7,122,014 B2 | 10/2006 | Palazzolo et al. |
| 7,190,999 B2 | 3/2007 | Geheb et al. |
| 7,650,181 B2 | 1/2010 | Freeman et al. |
| 7,747,319 B2 | 6/2010 | Freeman |
| 8,105,249 B2 | 1/2012 | Freeman |
| 8,428,672 B2 | 4/2013 | Sherman et al. |
| 8,478,401 B2 | 7/2013 | Freeman |
| 8,667,963 B2 | 3/2014 | Sherman et al. |
| 8,700,147 B2 | 4/2014 | Freeman |
| 8,738,129 B2 | 5/2014 | Packer et al. |
| 8,738,130 B2 | 5/2014 | Freeman et al. |
| 2001/0018562 A1 | 8/2001 | Sherman et al. |
| 2001/0039383 A1 | 11/2001 | Mohler |
| 2001/0047140 A1 | 11/2001 | Freeman |
| 2001/0047192 A1 | 11/2001 | Lasersohn et al. |

(56) References Cited

U.S. PATENT DOCUMENTS

| | | |
|---|---|---|
| 2001/0049545 A1 | 12/2001 | Lasersohn et al. |
| 2002/0032383 A1 | 3/2002 | Weil et al. |
| 2002/0072685 A1 | 6/2002 | Rymut et al. |
| 2002/0138122 A1 | 9/2002 | Worthen et al. |
| 2002/0165585 A1 | 11/2002 | Dupelle et al. |
| 2002/0173725 A1 | 11/2002 | Rock et al. |
| 2002/0193853 A1 | 12/2002 | Worthen et al. |
| 2003/0060723 A1 | 3/2003 | Joo et al. |
| 2003/0109790 A1 | 6/2003 | Stickney et al. |
| 2004/0039313 A1 | 2/2004 | Sherman et al. |
| 2004/0039419 A1 | 2/2004 | Stickney et al. |
| 2004/0039420 A1 | 2/2004 | Jayne et al. |
| 2004/0082888 A1 | 4/2004 | Palazzolo et al. |
| 2004/0210170 A1 | 10/2004 | Palazzolo et al. |
| 2004/0210171 A1 | 10/2004 | Palazzolo et al. |
| 2004/0267324 A1 | 12/2004 | Geheb et al. |
| 2005/0234515 A1 | 10/2005 | Freeman |
| 2005/0240234 A1 | 10/2005 | Joo et al. |
| 2005/0256415 A1 | 11/2005 | Tan et al. |
| 2005/0267536 A1 | 12/2005 | Freeman et al. |
| 2006/0167515 A1 | 7/2006 | Stickney et al. |
| 2006/0270952 A1 | 11/2006 | Freeman et al. |
| 2007/0060785 A1 | 3/2007 | Freeman |
| 2007/0169779 A1 | 7/2007 | Freeman |
| 2007/0219588 A1 | 9/2007 | Freeman |
| 2007/0225623 A1 | 9/2007 | Freeman |
| 2007/0272243 A1 | 11/2007 | Sherman et al. |
| 2009/0149903 A1 | 6/2009 | Freeman |
| 2010/0106208 A1 | 4/2010 | Freeman |
| 2010/0114219 A1 | 5/2010 | Stickney et al. |
| 2010/0121208 A1 | 5/2010 | Stickney et al. |
| 2010/0121392 A1 | 5/2010 | Stickney et al. |
| 2010/0160839 A1 | 6/2010 | Freeman et al. |
| 2010/0186742 A1 | 7/2010 | Sherman et al. |
| 2010/0221691 A1 | 9/2010 | Freeman et al. |
| 2010/0292544 A1 | 11/2010 | Sherman et al. |
| 2010/0292748 A9 | 11/2010 | Stickney et al. |
| 2011/0120471 A1 | 5/2011 | Freeman |
| 2011/0144708 A1 | 6/2011 | Joo et al. |
| 2011/0224587 A1 | 9/2011 | Freeman |
| 2011/0284004 A1 | 11/2011 | Silver et al. |
| 2012/0004582 A1 | 1/2012 | Palazzolo et al. |
| 2012/0016179 A1 | 1/2012 | Paradis et al. |
| 2012/0059292 A1 | 3/2012 | Freeman |
| 2012/0123223 A1 | 5/2012 | Freeman et al. |
| 2012/0123224 A1 | 5/2012 | Packer et al. |
| 2012/0302910 A1 | 11/2012 | Freeman et al. |
| 2013/0072830 A1 | 3/2013 | Illindala et al. |
| 2013/0289639 A1 | 10/2013 | Freeman |
| 2013/0296719 A1 | 11/2013 | Packer et al. |
| 2014/0052032 A1 | 2/2014 | Freeman et al. |
| 2014/0155793 A1 | 6/2014 | Illindala et al. |
| 2014/0180138 A1 | 6/2014 | Freeman et al. |
| 2014/0243914 A1 | 8/2014 | Freeman et al. |
| 2014/0257054 A1 | 9/2014 | Packer et al. |
| 2014/0296675 A1 | 10/2014 | Freeman et al. |

FOREIGN PATENT DOCUMENTS

| | | |
|---|---|---|
| EP | 1057498 A2 | 12/2000 |
| GB | 2150332 A | 6/1985 |
| WO | 84/01705 A1 | 5/1984 |
| WO | 93/22970 A1 | 11/1993 |
| WO | 97/05821 A1 | 2/1997 |
| WO | 01/22885 A1 | 4/2001 |

OTHER PUBLICATIONS

±5 g to ±50 g, Low Noise, Low Power, Single/Dual Axis iMEMS® Accelerometers (ADXL150/ADXL250-Specifications), Analog Devices, Inc., Rev. 0, 1998, 15 pages.

Iwata, et al., "Pattern Classification of the Phonocardiogram Using Linear Prediction Analysis," Medical & Biological Engineering and Computing 15(4):407-412, Jul. 1977.

Alt, et al., "Feasibility of Using Intracardiac Impedance Measurements for Capture Detection," Pacing and Clinical Electrophysiology 15:1873-1879, Nov., Part II, 1992.

Bahr, "Skills of Lay People in Checking the Carotid Pulse," Resuscitation 35:23-26, 1997.

Boggard, et al., "Assessment of the Haemodynamic Response to Exerise by Means of Electrical Impedance Cardiography: Method, Validation and Clinical Applications," Physiological Measurement 18:95-105, May 1997.

Bulgrin, et al., "Comparison of Short-time Fourier, Wavelet and Time-domain Analyses of Intracardiac Sounds," Biomedical Sciences Instrumentation 29:465-472, 1993, ISA Paper #93-059.

CardioDynamics, "What is BioZ® ICG Test?" http://www.cardiodynamics.com/cdpati10.html, Accessed Dec. 8, 2005.

CardioDynamics, BioZ Technology, "ICG Technology," http://www.cardiodynamics.com/cdprod40.html, Accessed Dec. 8, 2005.

Cobb, et al., "Influence of Cardiopulmonary Resuscitation Prior to Defibrillation in Patients With Out-of-Hospital Ventricular Fibrillation," JAMA 281:1182-1188, 1999.

Duda, et al., "Pattern Classification and Scene Analysis," Published by John Wiley & Sons, New York, 1973, pp. 1-482.

Eberle, et al., "Checking the Carotid Pulse Check: Diagnostic Accuracy of First Responders in Patients With and Without a Pulse," Resuscitation 33:107-116, 1996.

Farag, et al., "Detection of pulse and respiratory signals from the wrist using dry electrodes," Biomedical instrumentation technology Association for the Advancement of Medical Instrumentation, Jul./Aug. 1995, 5 pages.

Geddes, et al., "Applications of Ultrasound," Doppler: Principals of Applied Biomedical Instrumentation, 3rd Edition, John Wiley and Sons, New York, 1989, pp. 184-209.

Geddes, et al., "Cyclops Whistler—A Noninvasive Audible Monitor for the Amplitude of the Arterial Pulse," Cardiovcascular Engineering, vol. 5, No. 2, 2005, pp. 97-102.

Gravenstein, et al., "Monitoring Carbon Dioxide," $CO_2$ Gas Monitoring in in Clinical Practice, 2nd Edition, Butterworth-Heinemann, Boston, 1995, pp. 23-42.

Gulcur, et al., "Estimation of Systolic Blood Pressure from the Second Heart Sounds," 2nd International Biomedical Engineering Days, 1998, pp. 39-40.

Hasegawa, et al., "Delayed Timing of Heart and Arterial Sounds in Patients with Implanted Pacemakers," Journal of Thoracic and Cardiovascular Surgery 72(1):62-66, Jul. 1976.

Hoffman, et al., "Respiratory Monitoring With a New Impedance Plethysmograph," Anaesthesia 41:1139-1142, 1986.

Hu, et al., "A Study of Methods for Impedance Cardiography," Proceedings of the 19th International Conference—IEEE/EMBS, Chicago, Oct. 30-Nov. 2, 1997, pp. 2074-2077.

Johnston, et al., "The Transthoracic Impedance Cardiogram Is a Potential Haemodynamic Sensor for and Automated External Defibrillator," Europe Heart Journal 19:1879-1888, Dec. 1998.

Kassal, et al., "Polymer-Based Adherent Differential-Output Sensor for Cardiac Auscultation," Medical Electronics, Sep. 1994, pp. 54-63.

Kay, "Modern Spectral Estimation: Theory and Application," Prentice Hall, Englewood Cliffs, New Jersey, 1988, pp. 182-183.

Kubicek, et al., "Development and Evaluation of an Impedance Cardiographic System to Measure Cardiac Output and Other Cardiac Parameters," National Aeronautics and Space Administration (NASA), Jul. 1, 1968 to Jun. 30, 1969, 472 pages.

Kubicek, et al., "Development and Evaluation of an Impedance Cardiac Output System," Aerospace Medicine 37:1208-1212, Dec. 1966.

Kubicek, et al., "Impedance Cardiography as a Noninvasive Method of Monitoring Cardiac Function and Other Parameters of the Cardiovascular System," Annals of the New York Academy of Sciences 170, No. 2 (Jul. 1, 1970): pp. 724-732.

Lapostolle, et al., "Basic cardiac life support providers checking the carotid pulse: performance, degree of conviction, and influencing factors," Academy of Emergency Medicine, 2004; 11:878-880.

Lehner, et al., "Microcomputer System for Quanitification of the Phonocardiogram," Proceedings of the Seventh Annual Conference of the IEEE/Engineering in Medicine and Biology Society 2(2):849-854, 1986.

(56) References Cited

OTHER PUBLICATIONS

Luisada, "The First Heart Sound in Normal and Pathological Conditions," Japanese Heart Journal, 28(2):143-156, Mar. 1987.

Measurement Specialties, Inc., "Piezo Film Sensors Technical Manual," Internet Version, Aug. 1998, 89 pages.

Mehlsen, et al., "A Comparison of Systolic Time Intervals Measured by Impedance Cardiography and Carotid Pulse Tracing," Danish Medical Bulletin 37(1):93-95, Feb. 1990.

Muzi, et al., "Clinical Application of ECG R-Wave Triggered, Ensemble-Averaged Impedance Waveforms," Annual International Conference of the IEEE Engineering in Medicine and Biology Society 12(5):1991, 1990.

Ochoa, et al., "Competence of Health Professionals to Check the Carotid Pulse," Resuscitation 37:173-175, 1998.

Renevey, et al., "Wrist-located pulse detection using IR signals, activity and nonlinear artifact cancellation," 2001 Conference Proceedings of the 23rd Annual International Conference of the IEEE Engineering in Medicine and Biology Society, Istanbul, Turkey, Oct. 25-28, 2001, 4 pages.

Rosell, et al., "Signal-to-Motion Artifact Ratio Versus Frequency Impedance Pneumography," IEEE Transactions on Biomedical Engineering 42(3):321-323, Mar. 1995.

Stodieck, et al., "Relationships Between the Electrocardiogram and Phonocardiogram: Potential for Improved Heart Monitoring," ISA Transactions, 23(4):59-65, Apr. 1984.

Tibballs, et al., "Reliability of pulse palpation by health care personnel to diagnose pediatric cardiac arrest," Reesuscitation, 2009; 80:61-64.

Wang, et al., "Impedance Cardiac Profile Monitoring by a Modified Ensemble Averaging Technique," Proceedings of the IEEE Engineering in Medicine and Biology Society 10th Annual International Conference, New Orleans, 1:39-40, 1988.

Watanabe, et al., "Computer Analysis of the Exercise ECG: A Review," Progress in Cardiovascular Diseases XXII (6):423-446, May/Jun. 1980.

Woltjer, et al., "The Technique of Impedance Cardiography," European Heart Journal 18:1396-1403, Sep. 1997.

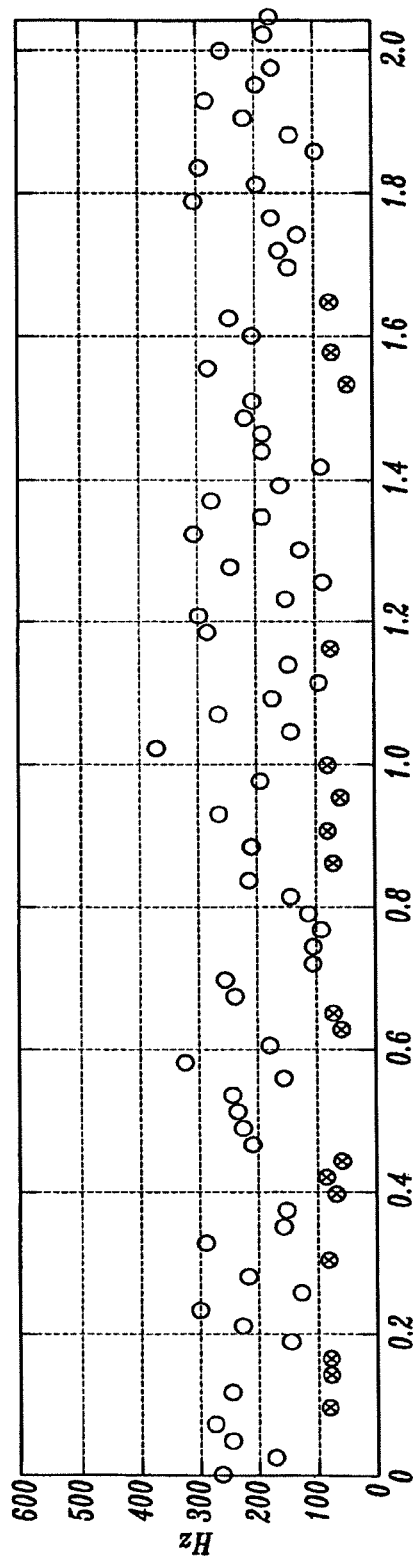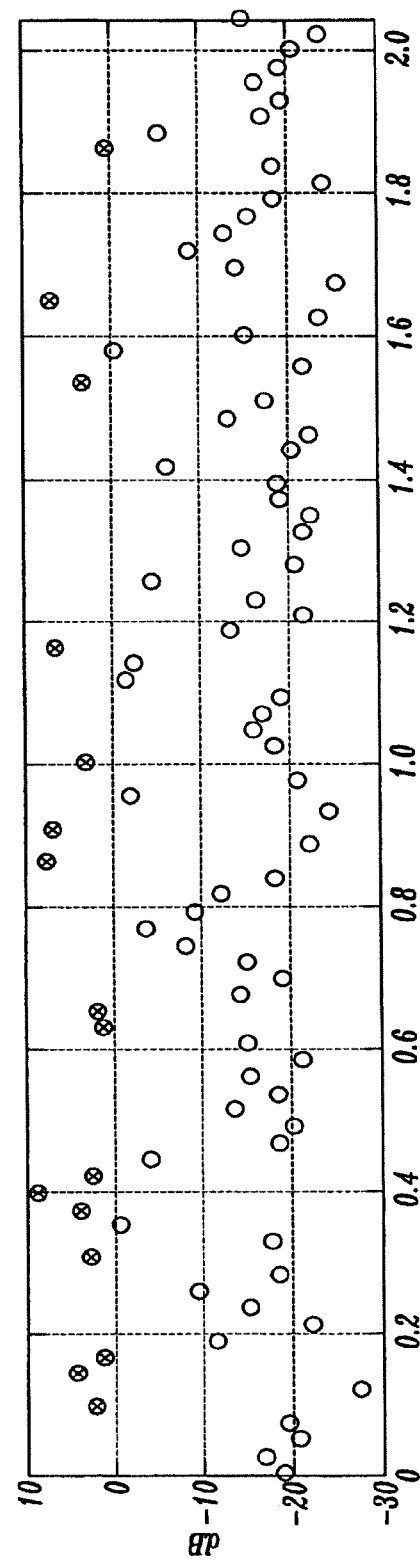
Fig.8B.
Fig.8C.

PULSE DETECTION APPARATUS, SOFTWARE, AND METHODS USING PATIENT PHYSIOLOGICAL SIGNALS

CROSS REFERENCE TO RELATED APPLICATIONS

This application is a continuation-in-part of U.S. patent application Ser. No. 13/267,783, filed Oct. 6, 2011, now U.S. Pat. No. 8,532,766, issued Sep. 10, 2013, which is a continuation of U.S. patent application Ser. No. 13/032,250, filed Feb. 22, 2011, now U.S. Pat. No. 8,239,024, which is a division of U.S. patent application Ser. No. 11/167,247, filed Jun. 27, 2005, now U.S. Pat. No. 7,917,209, which is a division of U.S. patent application Ser. No. 10/229,320, filed Aug. 26, 2002, now abandoned, which is a continuation-in-part of U.S. patent application Ser. No. 09/410,198, filed Sep. 30, 1999, now U.S. Pat. No. 6,440,082, and is a continuation-in-part of U.S. patent application Ser. No. 10/013,941, filed Dec. 6, 2001, now abandoned, all herein incorporated by reference.

FIELD OF THE INVENTION

The invention relates generally to the detection of cardiac activity in a patient, and more specifically, to the detection of a cardiac pulse and the use of pulse detection in delivering therapy.

BACKGROUND OF THE INVENTION

The presence of cardiac pulse, or heartbeat, in a patient is generally detected by palpating the patient's neck and sensing changes in the volume of the patient's carotid artery due to blood pumped from the patient's heart. A graph representative of the physical expansion and contraction of a patient's carotid artery during two consecutive pulses, or heartbeats, is shown at the top of FIG. 1. When the heart's ventricles contract during a heartbeat, a pressure wave is sent throughout the patient's peripheral circulation system. The carotid pulse shown in FIG. 1 rises with the ventricular ejection of blood at systole and peaks when the pressure wave from the heart reaches a maximum. The carotid pulse falls off again as the pressure subsides toward the end of each pulse.

The opening and closing of the patient's heart valves during a heartbeat causes high-frequency vibrations in the adjacent heart wall and blood vessels. These vibrations can be heard in the patient's body as heart sounds. A conventional phonocardiogram (PCG) transducer placed on a patient converts the acoustical energy of the heart sounds to electrical energy, resulting in a PCG waveform that may be recorded and displayed, as shown by the graph in the upper middle portion of FIG. 1. Conventional methods for detecting and displaying a PCG waveform are known in the art. See, e.g., U.S. Pat. Nos. 5,687,738 and 4,548,204.

As indicated by the PCG waveform shown in FIG. 1, a typical heartbeat produces two main heart sounds. The first heart sound, denoted S1, is generated by vibration generally associated with the closure of the tricuspid and mitral valves at the beginning of systole. Typically, the heart sound S1 is about 14 milliseconds long and contains frequencies up to approximately 500 Hz. The second heart sound, denoted S2, is generally associated with vibrations resulting from the closure of the aortic and pulmonary valves at the end of systole. While the duration of the second heart sound S2 is typically shorter than the first heart sound S1, the spectral bandwidth of the heart sound S2 is typically larger than that of S1.

An electrocardiogram (ECG) waveform describes the electrical activity of a patient's heart. The graph in the lower middle portion of FIG. 1 illustrates an example of an ECG waveform for two heartbeats and corresponds in time with the carotid pulse and PCG waveform. Referring to the first shown heartbeat, the portion of the ECG waveform representing depolarization of the atrial muscle fibers is referred to as the "P" wave. Depolarization of the ventricular muscle fibers is collectively represented by the "Q," "R," and "S" waves of the ECG waveform. Finally, the portion of the waveform representing repolarization of the ventricular muscle fibers is known as the "T" wave. Between heartbeats, the ECG waveform returns to an isopotential level.

Fluctuations in a patient's transthoracic impedance also correlate with blood flow that occurs with each cardiac pulse wave. The bottom graph of FIG. 1 illustrates an example of a filtered impedance signal for a patient in which fluctuations in impedance correspond in time with the carotid pulse, the PCG, and ECG waveforms.

The lack of a detectable cardiac pulse in a patient is a strong indicator of cardiac arrest. Cardiac arrest is a life-threatening medical condition in which the patient's heart fails to provide enough blood flow to support life. During cardiac arrest, the electrical activity may be disorganized (ventricular fibrillation), too rapid (ventricular tachycardia), absent (asystole), or organized at a normal or slow heart rate without sufficient blood flow (pulseless electrical activity). A caregiver may apply a defibrillation shock to a patient in ventricular fibrillation (VF) or ventricular tachycardia (VT) to stop the unsynchronized or rapid electrical activity and allow a perfusing rhythm to return. External defibrillation, in particular, is provided by applying a strong electric pulse to the patient's heart through electrodes placed on the surface of the patient's body. If a patient lacks a detectable pulse but has an ECG rhythm of asystole or pulseless electrical activity (PEA), conventional therapy may include cardiopulmonary resuscitation (CPR), which causes some blood flow.

Before providing defibrillation therapy or CPR to a patient, a caregiver must first confirm that the patient is in cardiac arrest. In general, external defibrillation is suitable only for patients that are unconscious, apneic (i.e., not breathing), pulseless, and in VF or VT. Medical guidelines indicate that the presence or absence of a pulse in a patient should be determined within 10 seconds. See, "American Heart Guidelines 2000 for Cardiopulmonary Resuscitation and Emergency Cardiovascular Care, Part 3: Adult Basic Life Support," Circulation 102 suppl. I: I-22-I-59, 2000.

Unfortunately, under the pressures of an emergency situation, it can be extremely difficult for first-responding caregivers with little or no medical training to consistently and accurately detect a cardiac pulse in a patient (e.g., by palpating the carotid artery) in a short amount of time such as 10 seconds. See, Eberle B., et al., "Checking the Carotid Pulse Diagnostic Accuracy of First Responders in Patients With and Without a Pulse" Resuscitation 33: 107-116, 1996. Nevertheless, because time is of the essence in treating cardiac arrest, a caregiver may rush the preliminary evaluation, incorrectly conclude that the patient has no pulse, and proceed to provide therapy; such as defibrillation, when in fact the patient has a pulse. Alternatively, a caregiver may incorrectly conclude that the patient has a pulse and erroneously withhold defibrillation therapy. A need therefore exists for a method and apparatus that quickly, accurately, and automatically determines the presence of a pulse in a patient, particularly to prompt a caregiver to provide appropriate therapy in an emergency situation.

SUMMARY OF THE INVENTION

The present invention provides methods and apparatus for determining the presence of a cardiac pulse in a patient by evaluating physiological signals in the patient. In one embodiment, a medical device constructed according to the invention includes a sensor system comprised of one or more sensors. The sensor system or any portion of it can be wearable by the patient or can be attachable to the patient in any other suitable manner. The sensor system is adapted to sense two or more different physiological signals in a patient. The two or more physiological signals are converted into digital physiological signal data that is processed by processing circuitry in the medical device. The processing circuitry is configured to evaluate the data from each physiological signal for a feature indicative of the presence of a cardiac pulse. Using these features, the medical device determines whether a cardiac pulse is present in the patient. The medical device further includes display that is used to automatically report whether a cardiac pulse is present in the patient. Exemplary embodiments of the invention discussed herein use physiological signals such as phonocardiogram (PCG) signals, electrocardiogram (ECG) signals, and patient impedance signals. Also, as noted herein, embodiments of the invention may use signals obtained from piezoelectric sensors and/or accelerometers placed on the patient's body.

In embodiments of the invention that evaluate ECG data, a feature indicative of the presence of a pulse may be determined based on the presence of a ventricular complex, such as a QRS complex, in the ECG data. Moreover, the presence of a ventricular complex in the ECG data may be used to select time segments of data from one or more of the other physiological signals that correspond in time with the ventricular complex. Identifying and evaluating physiological signal data based on the presence of a ventricular complex helps focus the evaluation of the physiological signal data to that data which are more likely to indicate the presence of a pulse.

Features thus obtained from the physiological signal data are evaluated to determine whether a cardiac pulse is present in the patient. A medical device constructed in accordance with the invention may further include a defibrillation pulse generator that is configured to automatically prepare a defibrillation pulse for delivery to the patient if the processing circuitry of the medical device determines that a cardiac pulse is not present in the patient. Alternatively, or in addition, the medical device may be configured to provide a message on its display prompting application of defibrillation electrodes to the patient if a cardiac pulse is determined not present. Further, a message may be displayed prompting delivery of chest compressions or cardiopulmonary resuscitation to the patient if a cardiac pulse is determined not present in the patient. A graph may be provided on the display showing a representation of at least one of the two or more physiological signals obtained from the patient.

Another embodiment of the present invention is an electrotherapy device that includes electrodes adapted to sense a physiological signal, such as a PCG signal, in a patient. The electrotherapy device can be wearable by the patient or can be attached to the patient in any suitable manner. Processing circuitry in the electrotherapy device is configured to analyze the PCG signal for a feature indicative of the presence of a cardiac pulse and determine whether a cardiac pulse is present based on the feature. If a cardiac pulse is determined not present, the processing circuitry prompts the delivery of electrotherapy to the patient. Where the electrotherapy is defibrillation therapy, the processing circuitry may be configured to report the return of spontaneous circulation in the patient if a cardiac pulse is determined to be present after the delivery of the defibrillation therapy.

The electrotherapy device may further sense ECG signals in the patient and analyze the ECG signals for ventricular fibrillation (VF), ventricular tachycardia (VT), asystole, and pulseless electrical activity (PEA). In one aspect, if the patient is determined to be pulseless and experiencing ventricular tachycardia, the electrotherapy device may prompt the delivery of defibrillation therapy. In another aspect, if the patient is determined to be pulseless and not in a VF, VT, or asystole condition, the processing circuitry may prompt delivery of electrotherapy that is specifically designed for pulseless electrical activity. The processing circuitry may also be configured to report whether the patient is in a VF, VT, asystole, or PEA condition, in addition to being in a pulseless condition.

In a further embodiment of the invention, the electrotherapy device also includes electrodes adapted to receive an impedance-sensing signal that has been communicated through the patient. The PCG and impedance signals are each analyzed for features indicative of the presence of a cardiac pulse in the patient. The electrotherapy device uses these features to determine the presence of a cardiac pulse. The impedance signal may also be used to determine the presence of respiration in the patient. If respiration is determined not present in the patient, the processing circuitry may prompt delivery of rescue breathing. If the patient is also determined to be pulseless, the processing circuitry may prompt the delivery of chest compressions or full cardiopulmonary resuscitation.

Yet another embodiment of the present invention provides an apparatus and method for delivering electrotherapy to a patient in which the electrotherapy is comprised of pacing stimuli and seeks capture of a cardiac pulse in the patient. The method includes delivering a pacing stimulus to the patient, sensing a physiological signal in the patient from the surface of the patient's body, determining whether a cardiac pulse occurred in the patient after delivery of the pacing stimulus, and increasing the current of further pacing stimuli to be delivered to the patient if a cardiac pulse did not occur in the patient after delivery of the pacing stimulus. For example, the physiological signal may be a PCG signal that is analyzed for the presence of a heart sound, the electrotherapy device determining whether a cardiac pulse occurred in the patient based on the presence of a heart sound. Consistent capture exhibited by a cardiac pulse may be required before making a final determination that capture of a cardiac pulse has been achieved.

Other applications and advantages of the present invention are apparent. For example, the invention may be implemented in an automated external defibrillator (AED). The AED can be a wearable AED that is worn by the patient or can be an AED that is not worn by the patient, but is rather used to monitor and apply defibrillation therapy to a patient. Still further, the invention can be a cardiac monitor that is either a wearable cardiac monitor that is worn by the patient or a cardiac monitor to which a patient is connected. The cardiac monitor embodiments do not provide defibrillation therapy, but can sense any combination of the disclosed physiological signs and can optionally prompt therapy and generate defibrillation (and other) therapy protocols. Embodiments of the invention intended for trained medical personnel may provide additional displays of the patient's physiological signal data for review.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 8B is a graph illustrating a series of frequencies of second peak energy values located in MEM spectra computed in accordance with the pulse detection process shown in FIG. 6 using the PCG data shown in FIG. 8A, in which the frequency values at or below a frequency of 100 Hz are marked with an "x";

FIG. 8C is a graph illustrating a series of second peak energy values located in MEM spectra computed in accordance with the pulse detection process shown in FIG. 9 using the PCG data shown in FIG. 8A, in which the second peak energy values exceeding 0 dB are marked with an "x";

DETAILED DESCRIPTION OF THE PREFERRED EMBODIMENT

Figure 1:
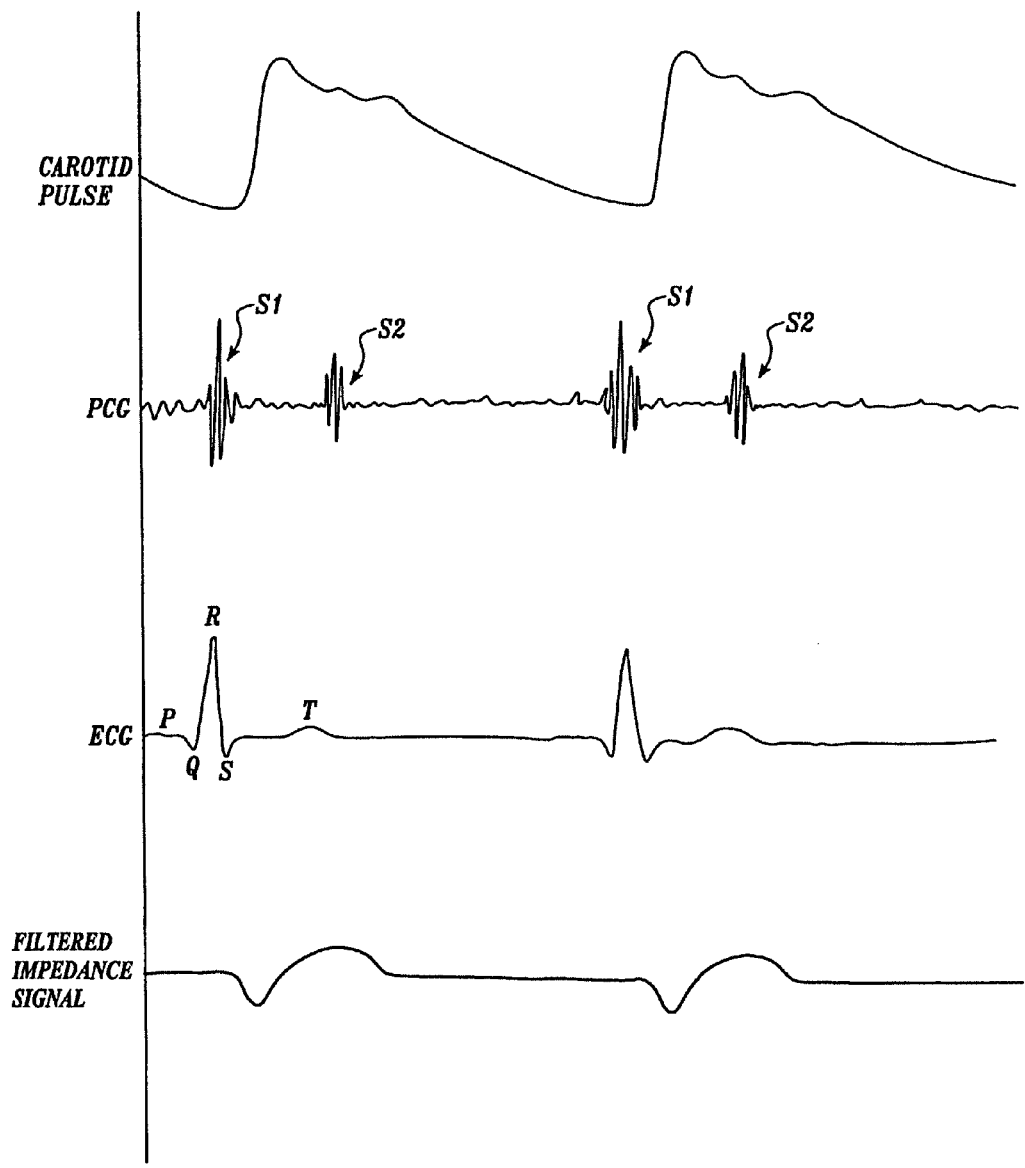
FIG. 1 is a pictorial diagram of a carotid pulse waveform, a phonocardiogram (PCG) waveform, an electrocardiogram (ECG) waveform, and a filtered transthoracic impedance signal for two consecutive heartbeats.
Figure 2:
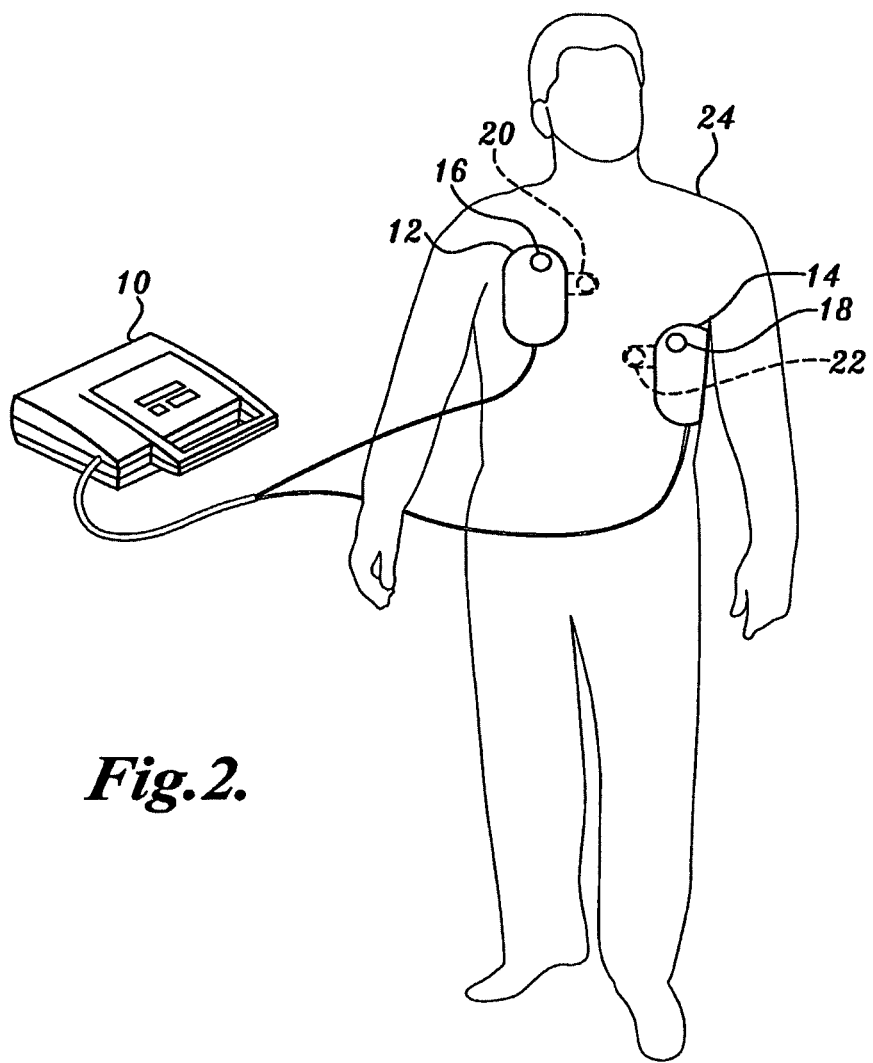
FIG. 2 is a pictorial diagram of a defibrillator and electrodes constructed in accordance with the present invention and attached to a patient.

The present invention may be implemented in a variety of applications. One particular implementation of the present invention is a defibrillator as illustrated in FIG. 2. In FIG. 2, the defibrillator 10 is shown connected to a patient 24 via defibrillation electrodes 12 and 14 placed on the skin of the patient 24. The defibrillator 10 uses the defibrillation electrodes 12 and 14 to deliver defibrillation pulses to the patient 24. The defibrillator 10 may also use the electrodes 12 and 14 to obtain ECG signals from the patient 24. Alternatively, the defibrillator can be a wearable defibrillator, in which case it would be worn by the patient and could function in the same manner as the defibrillator shown in FIG. 2.

FIG. 2 further illustrates sensing devices 16 and 18 placed on the patient 24. The sensing devices 16 and 18 are configured to detect a physiological signal in the patient, such as acoustical energy from heart sounds produced in the patient 24 or electrical energy that reflects a patient characteristic such as transthoracic impedance. In one exemplary embodiment discussed herein, the sensing devices 16 and 18 are configured to detect acoustical energy while the defibrillation electrodes 12 and 14 are used for assessing patient impedance. Acoustical energy sensed by the devices 16 and 18 is converted by the defibrillator 10 into digital phonocardiogram (PCG) data.

The sensing devices 16 and 18 may be integrated into or attached to the back of the electrodes 12 and 14. Alternatively, the sensing devices 16 and 18 may be embodied in flaps 20 and 22 that are connected to the electrodes 12 and 14. As another alternative, the sensing devices 16 and 18 may be attached to the patient 24 by separate wires (not shown).

In one embodiment of the invention, the sensing devices 16 and 18 are comprised of transducers with a piezoelectric membrane. The sensing devices 16 and 18 may alternatively be comprised of acoustic sensors known in the art, such as electronic microphones used in stethoscopes. Transducers and/or microphones suitable for use in the present invention for detecting heart sounds are described, for example, in U.S. Pat. Nos. 4,446,873 and 5,825,895.

A device constructed in accordance with the present invention may also use measurements of a patient's transthoracic impedance, separately or in connection with detecting heart sounds, to determine the presence of a cardiac pulse in a patient. In that regard, the electrodes 12, 14 may be configured to communicate an impedance-sensing signal through the patient 24. The impedance-sensing signal is used by the defibrillator 10 to measure the patient's impedance.

A preferred embodiment of the invention uses a high-frequency, low-level constant current technique to measure the patient's transthoracic impedance, though other known impedance measuring techniques may be used. A signal generator included in the defibrillator 10 produces a low-amplitude, constant current, high-frequency signal (typically sinusoidal or square). The signal is preferably generated having a frequency in the range of 10 kHz-100 kHz and causes a current to flow between the electrodes 12 and 14. The current flow causes a voltage to develop across the patient's body that is proportional to the product of the patient's impedance and the applied current. To calculate the patient's impedance, the impedance measuring component in the defibrillator 10 divides the measured sensing voltage by the applied current. Of course, since the measured voltage is linearly related to the patient's impedance, the impedance signal data used herein may be a calculated impedance signal or the measured voltage signal.

While embodiments of the invention specifically described herein are shown implemented in a defibrillator 10, the present invention is not limited to such specific type of application. Those of ordinary skill in the art will recognize that the advantages of the invention may similarly be achieved by implementing the present invention in cardiac monitors and other types of medical equipment that do not necessarily provide defibrillation therapy.

Figure 3:
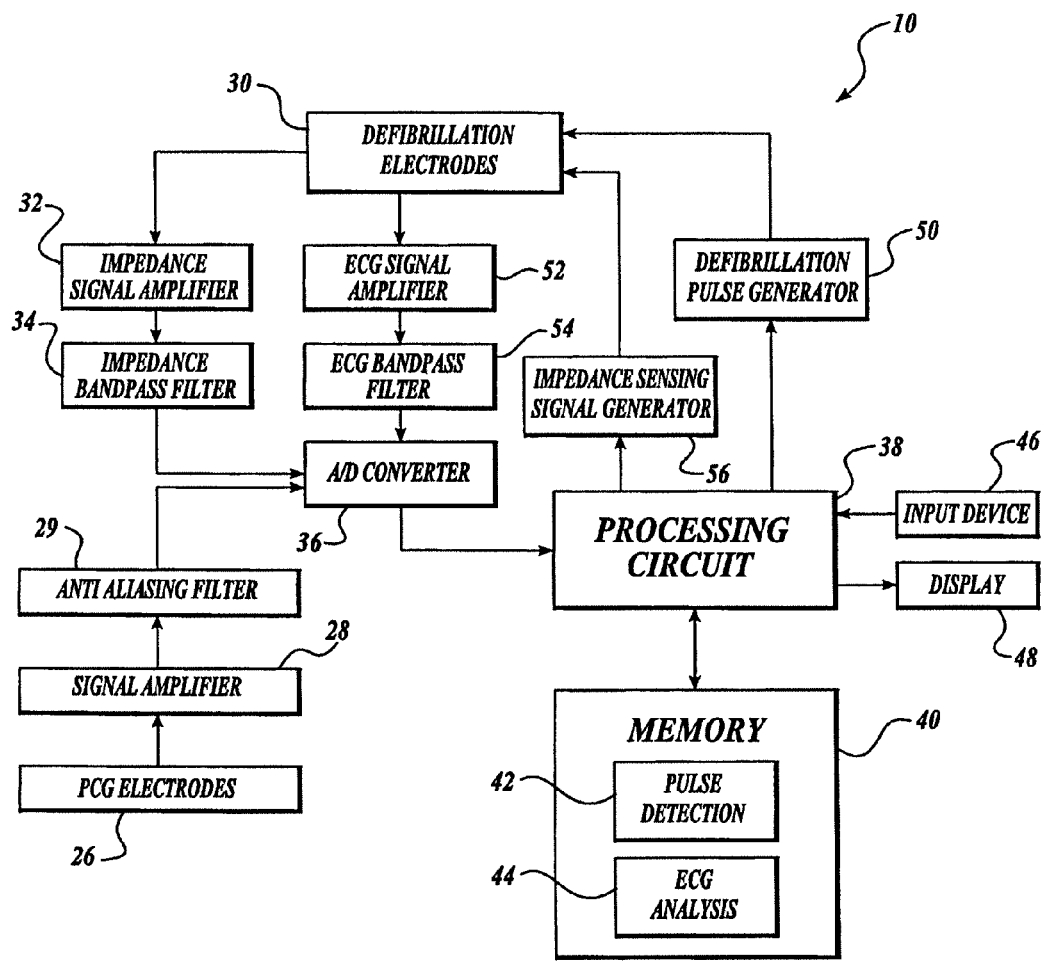
FIG. 3 is a block diagram of the major components of a defibrillator as shown in FIG. 2.

Prior to discussing various pulse detection processes that the defibrillator 10 may implement in accordance with the present invention, a brief description of certain major components of the defibrillator 10 is provided. Referring to FIG. 3, the defibrillator 10 includes defibrillation electrodes 30 (e.g., electrodes 12, 14 described above in FIG. 2). An impedance-sensing signal generator 56 communicates an impedance-sensing signal through the patient via the electrodes 30. A signal amplifier 32 receives the impedance-sensing signal from the electrodes 30 and amplifies the signal to a level appropriate for digitization by analog-to-digital (A/D) converter 36. Prior to A/D conversion, a bandpass filter 34 filters the amplified impedance-sensing signal to isolate the portion of the signal that most closely reveals fluctuations due to blood flow from cardiac pulses. In one embodiment of the invention, the bandpass filter 34 is a 1-10 Hz bandpass filter. Fluctuations in the impedance signal below 1 Hz are believed more likely to be caused by respiration in the patient, and not blood flow. Accordingly, the bandpass filter attenuates that component of the impedance signal. The portion of the impedance signal exceeding 10 Hz is believed more likely affected by surrounding noise and is likewise filtered out.

The filtered impedance signal is delivered to the A/D converter 36 which converts the impedance signal into digital impedance data for further evaluation. The bandpass filter 34 or other filter may be provided to reduce any aliasing introduced in the impedance signal by the A/D converter 36. The parameters of such filtering depend, in part, on the sampling rate of the A/D converter. Bandpass and antialiasing filters, as well as A/D converters, are well-known in the art, and may be implemented in hardware or software, or a combination of both. For example, a preferred embodiment uses a hardware lowpass filter on the impedance signal before the A/D converter 36, and then a software highpass filter on the digital impedance data after the A/D conversion. Another preferred embodiment additionally uses a software lowpass filter after the A/D conversion to further limit the bandwidth of the impedance signal. The A/D converter 36 delivers the digital impedance signal data to a processing circuit 38 for evaluation.

The processing circuit 38 evaluates the impedance signal data for the presence of a cardiac pulse. The processing circuit 38 is preferably comprised of a computer processor that operates in accordance with programmed instructions stored in a memory 40 that implement a pulse detection process 42, described in more detail below. The processing circuit 38 may also store in the memory 40 the impedance signal data obtained from the patient, along with other event data and ECG signal data. The memory 40 may be comprised of any type or combination of types of storage medium, including, for example, a volatile memory such as a dynamic random access memory (DRAM), a non-volatile static memory, or computer-readable media such as a magnetic tape or disk or optical storage unit (e.g., CD-RW or DVD) configured with permanent or removable media.

The processing circuit 38 may report the results of the pulse detection process to the operator of the defibrillator 10 via a display 48. The processing circuit 38 may also prompt actions (e.g., CPR) to the operator to direct the resuscitation effort. The display 48 may include, for example, lights, audible signals, alarm, printer, tactile response, and/or display screen. The processing circuit 38 may also receive input from the operator of the defibrillator 10 via an input device 46. The input device 46 may include one or more keys, switches, buttons, dials, or other types of user input devices.

The defibrillator 10 shown in FIG. 3 is also capable of sensing a patient's heart sounds using PCG electrodes 26 (e.g., sensing devices 16 and 18, as described above in reference to FIG. 2). The PCG electrodes 26 provide the sensed heart sound signals, or PCG signals, to a signal amplifier 28 that amplifies the PCG signals to a level sufficient for the defibrillator 10 to further analyze the PCG signals.

The signal amplifier 28 provides the amplified PCG signals to an anti-aliasing filter 29. The anti-aliasing filter 29 is designed to reduce aliasing introduced in the PCG signals by the analog-to-digital (A/D) converter 36. The bandwidth of the anti-aliasing filter 29 depends, in part, on the .sampling rate of the A/D converter 36. Anti-aliasing filters and A/D converters are well-known in the art and are readily available in off-the-shelf devices. Alternative embodiments of the defibrillator 10 may include additional signal amplification or signal filtering to adapt the defibrillator 10 for use in particular environments.

The A/D converter 36 converts the PCG signals into digitized PCG data and provides the PCG data to the processing circuit 38 for evaluation. The processing circuit 38 evaluates the PCG data using a pulse detection process described below in more detail. Programmed instructions 42 stored in the memory 40 may be used to implement the pulse detection process. Preferably, the processing circuit 38 also stores the PCG data in the memory 40.

The defibrillation electrodes 30 may further be used to sense the patient's electrocardiogram (ECG) signals. ECG signals obtained from the patient are amplified by the ECG signal amplifier 52 and filtered by the ECG bandpass filter 54 in a conventional manner. The A/D converter 36 converts the ECG signals into digitized ECG data and provides the ECG data to the processing circuit 38 for evaluation.

Preferably, the processing circuit 38 evaluates the ECG signals in accordance with programmed instructions 44 stored in the memory 40 that carry out an ECG evaluation process to determine whether a defibrillation shock should be provided. A suitable method for determining whether to apply a defibrillation shock is described in U.S. Pat. No. 4,610,254, which is assigned to the assignee of the present invention and incorporated by reference herein. If the processing circuit 38 determines that immediate delivery of a defibrillation pulse is appropriate, the processing circuit 38 instructs a defibrillation pulse generator 50 to prepare to deliver a defibrillation pulse to the patient. In that regard, the defibrillation pulse generator 50 uses an energy source (e.g., a battery) to charge one or more defibrillation capacitors in the defibrillator 10.

When the defibrillation charge is ready for delivery, the processing circuit 38 advises the operator via the display 48 that the defibrillator 10 is ready to deliver the defibrillation pulse. The processing circuit 38 may ask the operator to initiate the delivery of the defibrillation pulse. When the operator initiates delivery of the defibrillation pulse (e.g., via the input device 46), the processing circuit 38 instructs the defibrillation pulse generator 50 to discharge through the patient the energy stored in the defibrillation capacitors (via the defibrillation electrodes 30). Alternatively, the processing circuit 38 may cause the defibrillation pulse generator 50 to automatically deliver the defibrillation pulse when specified conditions (e.g., expiration of a predetermined period of time, acceptable measured patient impedance, etc.) are met.

In some circumstances, it may be preferable to apply CPR to the patient before defibrillation even though cardiac conditions, such as VF, are detected, especially for patients in whom defibrillation is initially unlikely to succeed. See L. Cobb et al., "Influence of Cardiopulmonary Resuscitation Prior to Defibrillation in Patients With Out-of-Hospital Ventricular Fibrillation" JAMA 281:1182-1188 (1999), incorporated by reference herein. Thus, if desired, the defibrillator 10 may recommend the application of chest compressions or CPR in situations where a cardiac pulse is not detected and the ECG reveals a cardiac rhythm for which immediate treatment by defibrillation therapy is not indicated.

While FIG. 3 illustrates certain major components of the defibrillator 10, those having ordinary skill in the art will appreciate that the defibrillator 10 may contain more or fewer components than those shown. The disclosure of a preferred embodiment of the defibrillator 10 does not require that all of these general conventional components be shown. It will further be appreciated that aspects of the invention may be implemented in a cardiac monitor having essentially the same components as the defibrillator 10 shown in FIG. 3, except that the cardiac monitor does not have the components necessary for delivering a defibrillation pulse. Furthermore, some or all of the programmed instructions 44 may be implemented in hardware as an alternative to software instructions stored in the memory 40. Still further, the defibrillator shown in FIG. 3 and the cardiac monitor embodiments may be wearable by the patient.

In one aspect, the pulse detection process conducted by the processing circuit 38 may analyze the patient's PCG data to determine whether heart sounds S1 and/or S2 are present. The presence of heart sounds S1 and/or S2 are used as an indication of the presence of a cardiac pulse in the patient. In another aspect, the pulse detection process may analyze the patient's impedance signal data to determine the presence of a cardiac pulse. The pulse detection process preferably uses a portion of the impedance-sensing signal whose frequency range is most likely to reveal fluctuations indicating the presence of a cardiac pulse in the patient. Characteristic fluctuations in patient impedance associated with a cardiac pulse are used as an indication of the presence of a cardiac pulse. In yet another aspect, the pulse detection process may analyze multiple physiological signals. For example, the pulse detection process may analyze both PCG data for heart sounds and impedance signal data for characteristic fluctuations in a combined manner to determine the presence of a cardiac pulse.

Figure 4:
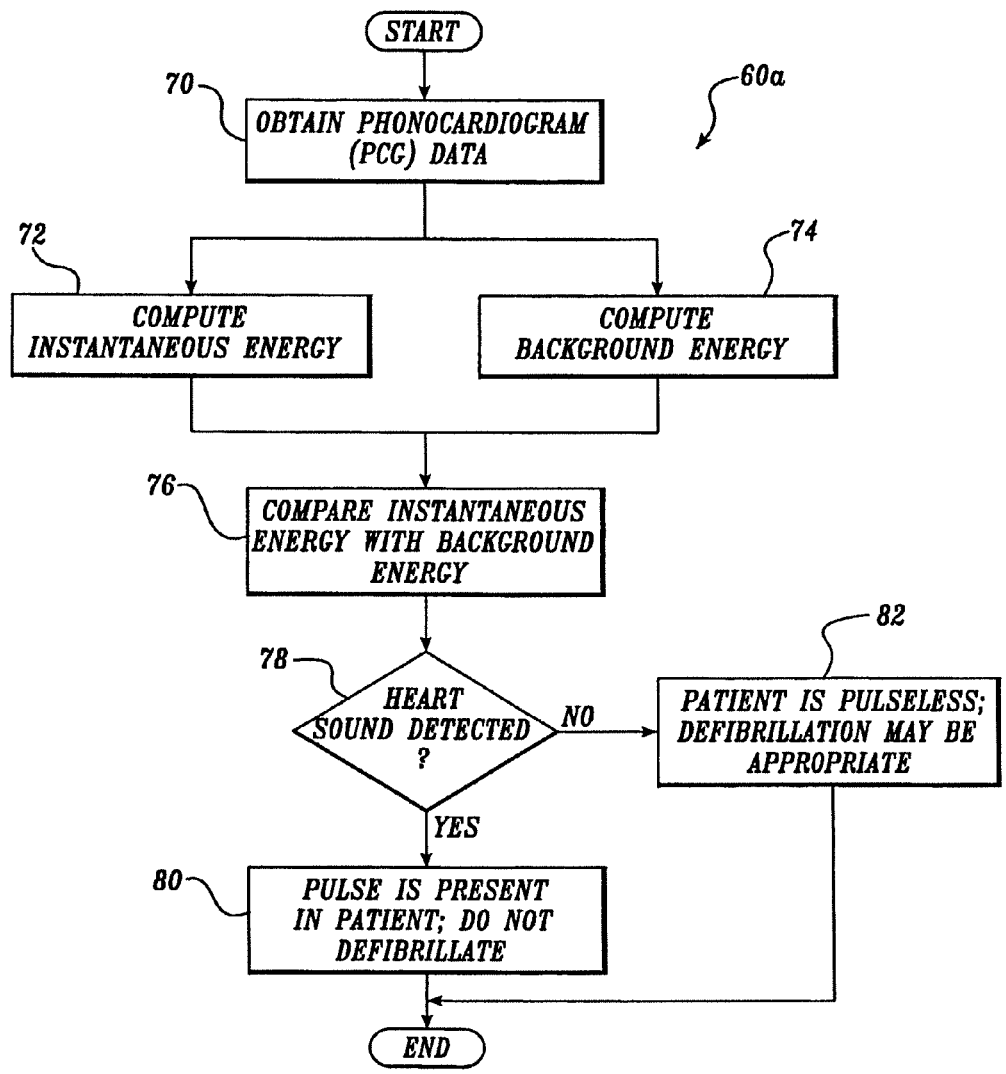
FIG. 4 is a flow diagram of a pulse detection process performed by a defibrillator as shown in FIG. 2, in which a temporal energy analysis of PCG data is performed.

FIG. 4 illustrates a pulse detection process 60a that analyzes a temporal energy in the PCG data. The pulse detection process 60a begins at block 70 by obtaining PCG data from a patient. As noted earlier, PCG signals received from PCG sensing devices (e.g., sensing devices 16 and 18 in FIG. 2) placed on the patient are converted into digital PCG data.

The pulse detection process 60a evaluates the PCG data for at least one feature indicative of the presence of a heart sound. In blocks 72 and 74, the pulse detection process 60a preferably calculates estimates of the instantaneous energy and background energy in the PCG data. As shown in FIG. 4, the estimated instantaneous energy may be calculated in block 72 simultaneously with the calculation of estimated background energy in block 74. Alternatively, the calculation of estimated instantaneous energy in block 72 may be performed prior to or after the calculation of estimated background energy in block 74.

The estimated instantaneous energy is calculated in block 72, preferably using a set of PCG data obtained from the patient during a predetermined time window. One exemplary embodiment of the invention uses a time window of 20 milliseconds in length, though a longer, shorter, or shifted time window may be used for estimating the instantaneous energy. The estimated instantaneous energy may be calculated by squaring and summing each of the PCG data values in the predetermined time window.

The estimated background energy is calculated in block 74, preferably using a set of PCG data obtained in an earlier predetermined time window. One exemplary embodiment of the invention calculates the estimated background energy using PCG data in a 100 millisecond time window commencing 220 milliseconds prior to the current time. The PCG data within the earlier time window may also be squared and summed to produce the estimated background energy. Furthermore, other time window lengths and starting points may be used.

The estimated instantaneous energy and background energy are next compared at block 76 to determine a relative change in energy in the PCG data. The relative change in energy is used by the pulse detection process 60a as a feature indicative of the presence of a heart sound. If the relative change in energy between the estimated instantaneous energy and the estimated background energy exceeds a predetermined threshold, the pulse detection process 60a determines that a heart sound was detected. Note that the background and instantaneous energies should previously be normalized for purposes of comparison to each other. For example, if squaring and summing is used and one energy uses a 100 ms time window and the other energy uses a 20 ms time window, the result of the energy using a 100 ms time window should be divided by 5 so it can be properly compared against the result from a 20 ms time window.

As discussed earlier, the present invention uses the detection of a heart sound as an indication of the presence of a cardiac pulse in the patient. In decision block 78, if a heart sound was detected, the pulse detection process 60a proceeds to block 80 and reports the presence of a cardiac pulse in the patient (thus indicating that defibrillation therapy for the patient is not advised). Otherwise, if a heart sound is not detected, the pulse detection process 60a determines in block 82 that the patient is pulseless and that defibrillation therapy may be appropriate. A defibrillator 10 implementing the pulse detection process 60a may then proceed to determine whether defibrillation therapy is appropriate, e.g., by obtaining and processing ECG data from the patient as described in U.S. Pat. No. 4,610,254, referenced earlier and incorporated herein by reference.

In a further embodiment of the invention, the pulse detection process 60a may be repeated over a specified time interval or for a specified number of repetitions to produce a series of determinations of whether a heart sound is present in the patient. The time windows for computing the estimated instantaneous energy and background energy are shifted to correspond with each instance of time in which the pulse detection process 60a is performed. The pulse detection process 60a may require a specified number of heart sound detections before determining that a cardiac pulse is present in the patient.

Figure 5A:
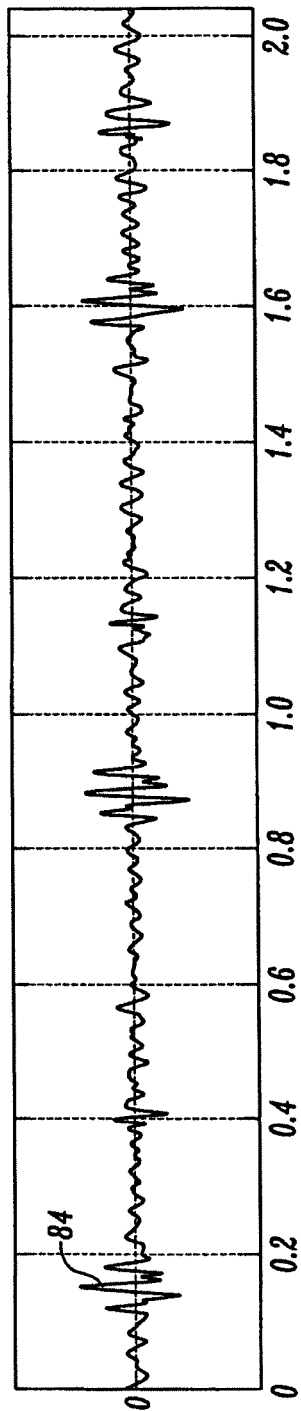
FIG. 5A is a graph illustrating a PCG waveform of raw PCG data collected from a patient.
Figure 5B:
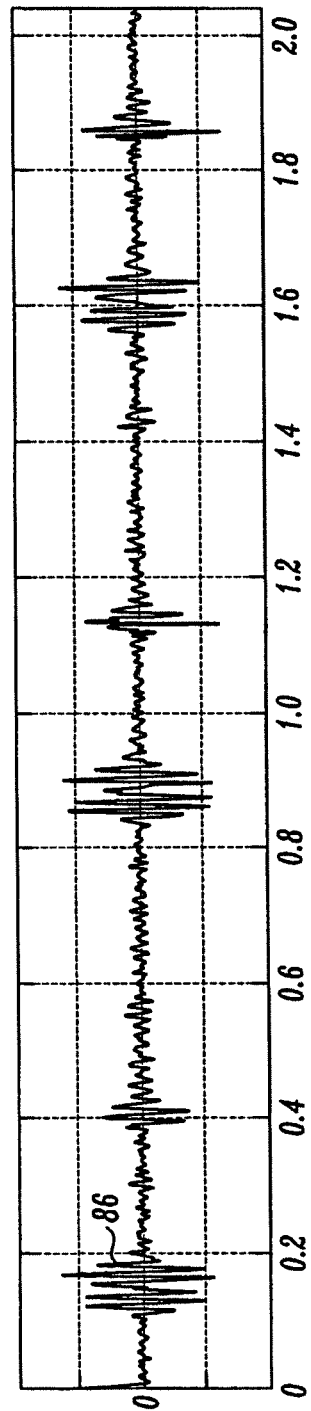
FIG. 5B is a graph illustrating a filtered version of the PCG waveform shown in FIG. 5A.

FIGS. 5A-5D illustrate a representative example of the processing performed by the pulse detection process 60a. In particular, FIG. 5A is a graph showing a PCG waveform 84 of raw PCG data as collected in block 70 (FIG. 4) from a patient. As noted above, the PCG data may be filtered to reduce noise and other signal contaminants. A filtered version of the PCG waveform 86 is shown in FIG. 5B.

Figure 5C:
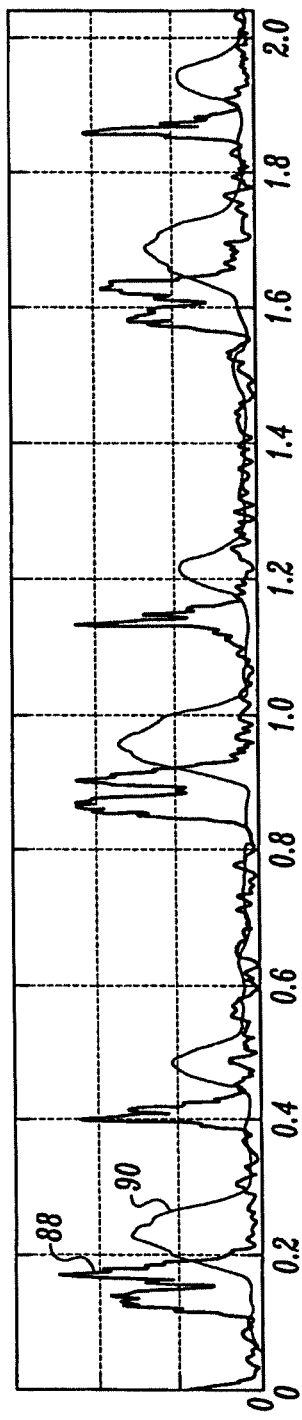
FIG. 5C is a graph illustrating an instantaneous, energy waveform and the background energy waveform computed from the data in the PCG waveform shown in FIG. 5B in accordance with the pulse detection process shown in FIG. 4.

FIG. 5C illustrates a waveform 88 depicting an estimated instantaneous energy in the PCG as calculated in block 72 of the pulse detection process 60a. The waveform 90 depicts an estimated background energy as calculated in block 74 of the pulse detection process 60a. Because the calculation of background energy 90 uses PCG data obtained in an earlier time window than the PCG data used to calculate instantaneous energy 88, the rise and fall of the background energy waveform 90 follows the rise and fall of the instantaneous energy waveform 88.

Figure 5D:
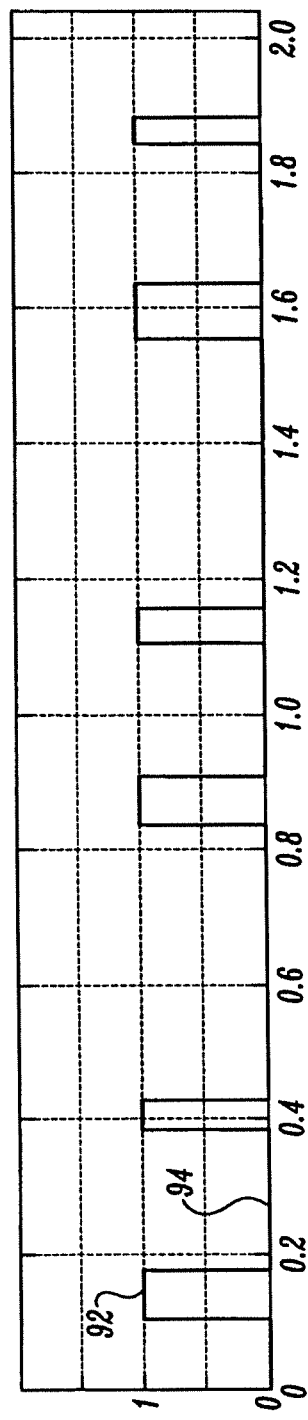
FIG. 5D is a graph illustrating the results of a comparison of the instantaneous energy and the background energy shown in FIG. 5C in accordance with the pulse detection process shown in FIG. 4.

The comparison performed in block 76 of the pulse detection process 60a may produce a result as illustrated in FIG. 5D. During the time in which the instantaneous energy 88 exceeds the background energy 90 by a predetermined threshold, the comparison performed in block 76 returns a "1" (signifying the detection of a heart sound), as noted by reference numeral 92. The predetermined threshold may be adjusted to achieve a desired sensitivity and specificity of detection. When the relative change in energy between the instantaneous energy 88 and the background energy 90 does not exceed the predetermined threshold, the comparison performed in block 76 returns a "0", as noted by reference number 94, signifying that a heart sound was not detected.

Figure 6:
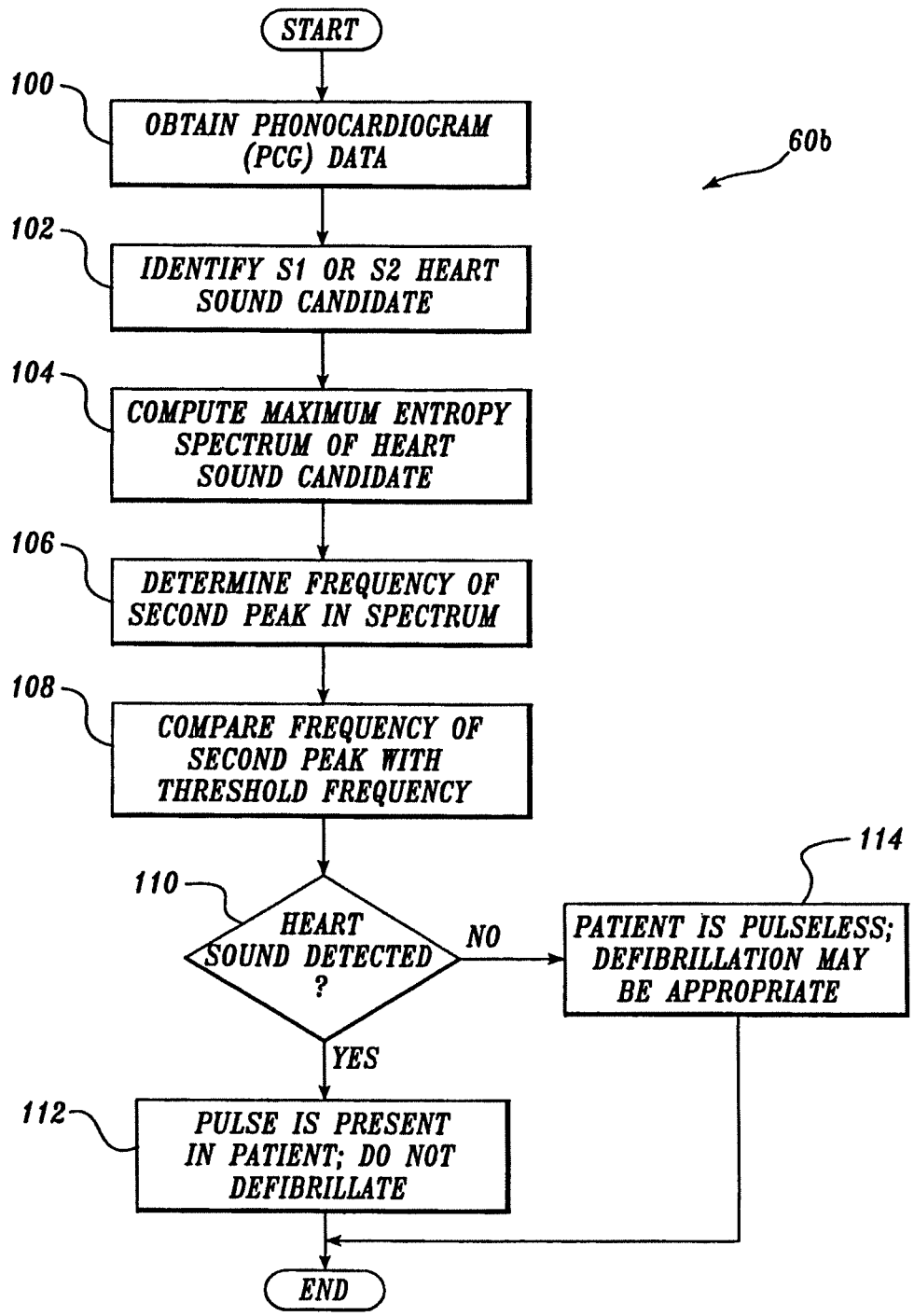
FIG. 6 is a flow diagram of another pulse detection process performed by a defibrillator as shown in FIG. 2, in which a spectral peak frequency analysis of PCG data is performed.

FIG. 6 illustrates another pulse detection process 60b. As with the detection process 60a, the detection process 60b analyzes PCG data to detect heart sounds in a patient. The detection process 60b, however, focuses on a spectral energy analysis of the PCG data (as compared to the temporal energy analysis performed in the detection process 60a).

The pulse detection process 60b begins at block 100 by obtaining PCG data from the patient in a manner as discussed above with respect to block 70 (FIG. 4). In block 102, the PCG data is preferably analyzed to identify a set of PCG data that likely contains an S1 or S2 heart sound. In that regard, an S1 or S2 heart sound candidate may be identified by using the temporal energy comparison discussed in block 76 of the pulse detection process 60a. When the estimated instantaneous energy exceeds the estimated background energy by a predetermined threshold, the energy comparison suggests that a potential S1 or S2 candidate has been detected. Alternatively, a set of PCG data containing a heart sound may be identified by evaluating the patient's ECG data for the occurrence of an R-wave. The timing of an S1 or S2 heart sound in relation to an R-wave is generally known in the art and may be used to predict the timing of a heart sound candidate in the PCG data. Other embodiments of the invention may compute an energy spectrum without first identifying candidate PCG data, e.g., by continuously computing an energy spectrum using the most current PCG data as the candidate data.

Next, in block 104, the pulse detection process 60b computes an energy spectrum of the heart sound candidate, preferably using a maximum entropy method, though other spectral calculations may be used. Computing an energy spectrum using a maximum entropy method ("MEM spectrum") is well-known in the art. See, e.g., Modern Spectral Estimation: Theory and Application, by Stephen M. Kay, published by Prentice Hall of Englewood Cliffs, N.J., beginning at p. 182, and incorporated herein by reference. An MEM spectrum typically appears much smoother than an energy spectrum produced by Fourier transform techniques.

Figure 7:
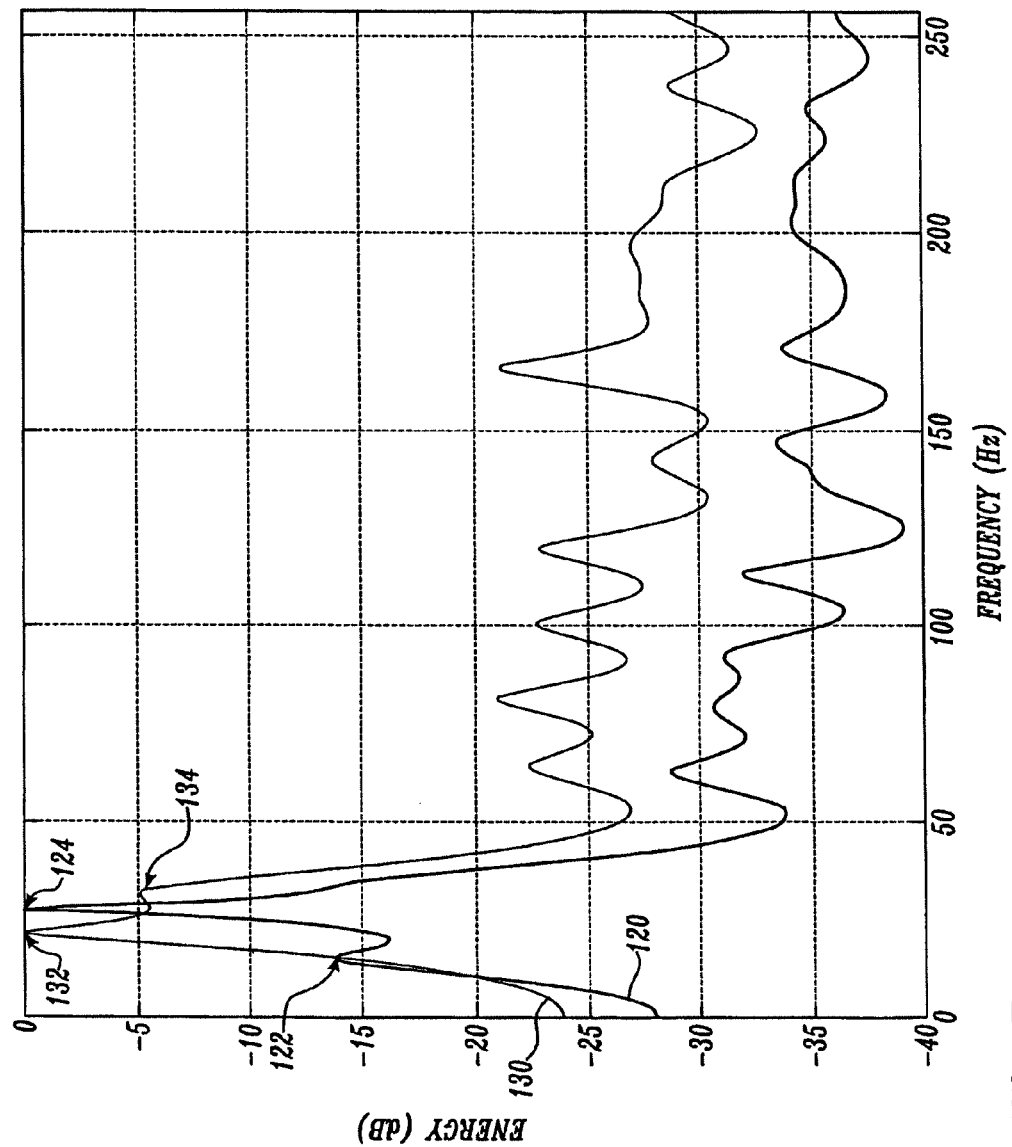
FIG. 7 is a graph illustrating two energy spectra calculated from PCG data using a maximum entropy method ("MEM spectra") in accordance with the pulse detection process shown in FIG. 6.

FIG. 7 illustrates a representative MEM spectrum 120 for an interval of PCG data containing an S1 heart sound. FIG. 7 also illustrates a representative MEM spectrum 130 for a set of PCG data containing an S2 heart sound. The MEM spectrum 120 includes a number of peak energy values, including the first two peak values 122 and 124. Likewise, the MEM spectrum 130 includes a number of peak energy values, including the first two peak values 132 and 134. The MEM spectrum 120 or 130, whichever is used, may be normalized by removing a baseline (e.g., DC) energy value across the MEM spectrum.

As discussed below in more detail, the frequency of a peak energy value in the energy spectrum is used as a feature indicative of the presence of a heart sound, and is evaluated against a predetermined threshold frequency value to decide whether a heart sound is detected. The pulse detection process 60b shown in FIG. 6 evaluates the second peak energy value occurring in the energy spectrum measured from DC, e.g., the second peak value 124 in the MEM spectrum 120, or the second peak value 134 in the MEM spectrum 130.

In block 106 (FIG. 6), the pulse detection process 60b evaluates the energy values in the MEM spectrum to determine the frequency of the second peak in the MEM spectrum. For example, if the pulse detection process 60b evaluates MEM spectrum 120, the frequency of the second peak 124 is determined. A similar analysis applied to the MEM spectrum 130 determines the frequency of the second peak 134.

In block 108, the frequency of the second peak 124 or 134 is compared with a predetermined threshold frequency to decide whether a heart sound is detected. For example, if the frequency of the second peak 124 or 134 is less than or equal to a threshold frequency, e.g., 100 Hz, the pulse detection process 60b determines that a heart sound was detected. Alternative embodiments of the invention may use values other than 100 Hz for the predetermined threshold frequency.

If a heart sound was detected, the pulse detection process 60b proceeds from decision block 110 to block 112 and determines that a pulse is present in the patient, thus advising against application of a defibrillation pulse. If, in decision block 110, a heart sound was not detected, the pulse detection process 60b determines in block 114 that the patient is pulseless and that defibrillation may be appropriate for the patient. In that case, further signal processing of ECG data obtained from the patient is preferably performed to determine the applicability of defibrillation therapy, e.g., as described in U.S. Pat. No. 4,610,254, referenced earlier.

Figure 8A:
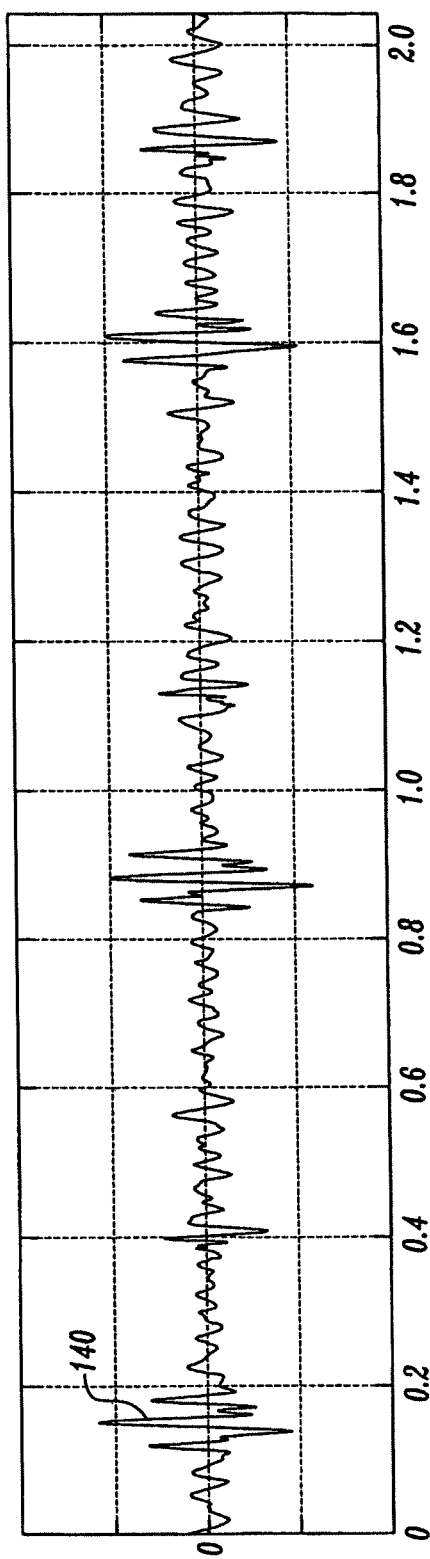
FIG. 8A is a graph illustrating a PCG waveform of raw PCG data collected from a patient.

One example illustrating the processing performed by the pulse detection process 60b is shown in FIGS. 8A and 8B. FIG. 8A is a graph depicting a PCG waveform 140 of raw PCG data obtained from a patient in a manner as discussed above in regard to block 100 (FIG. 6). Although not shown in FIG. 8, the PCG waveform 140 may be filtered to reduce noise and other signal contaminants (e.g., as described earlier in reference to FIG. 5B).

For purposes of demonstrating the detection of heart sounds in the detection process 60b, an MEM spectrum of the data in the PCG waveform 140 is computed for a number of instances in time, and the frequency of the second peak of each MEM spectrum is identified, as shown by the circles in FIG. 8B, without regard to whether the selected instance of time corresponds with a heart sound candidate. Of course, in actual operation where results are needed for immediate and accurate evaluation of a patient, it is preferable that the PCG data first be screened for heart sound candidates.

In FIG. 8B, the circles enclosing an "x" identify the MEM spectra that, for this example, have a second peak located at or below a threshold frequency of 100 Hz. Note that, for the most part, the circles with an "x" in FIG. 8B correspond in time with the heart sounds evident in the PCG waveform 140 shown in FIG. 8A. For each circled "x," the pulse detection process 60*b* decides that a heart sound, and thus a pulse, is present in the patient.

Figure 9:
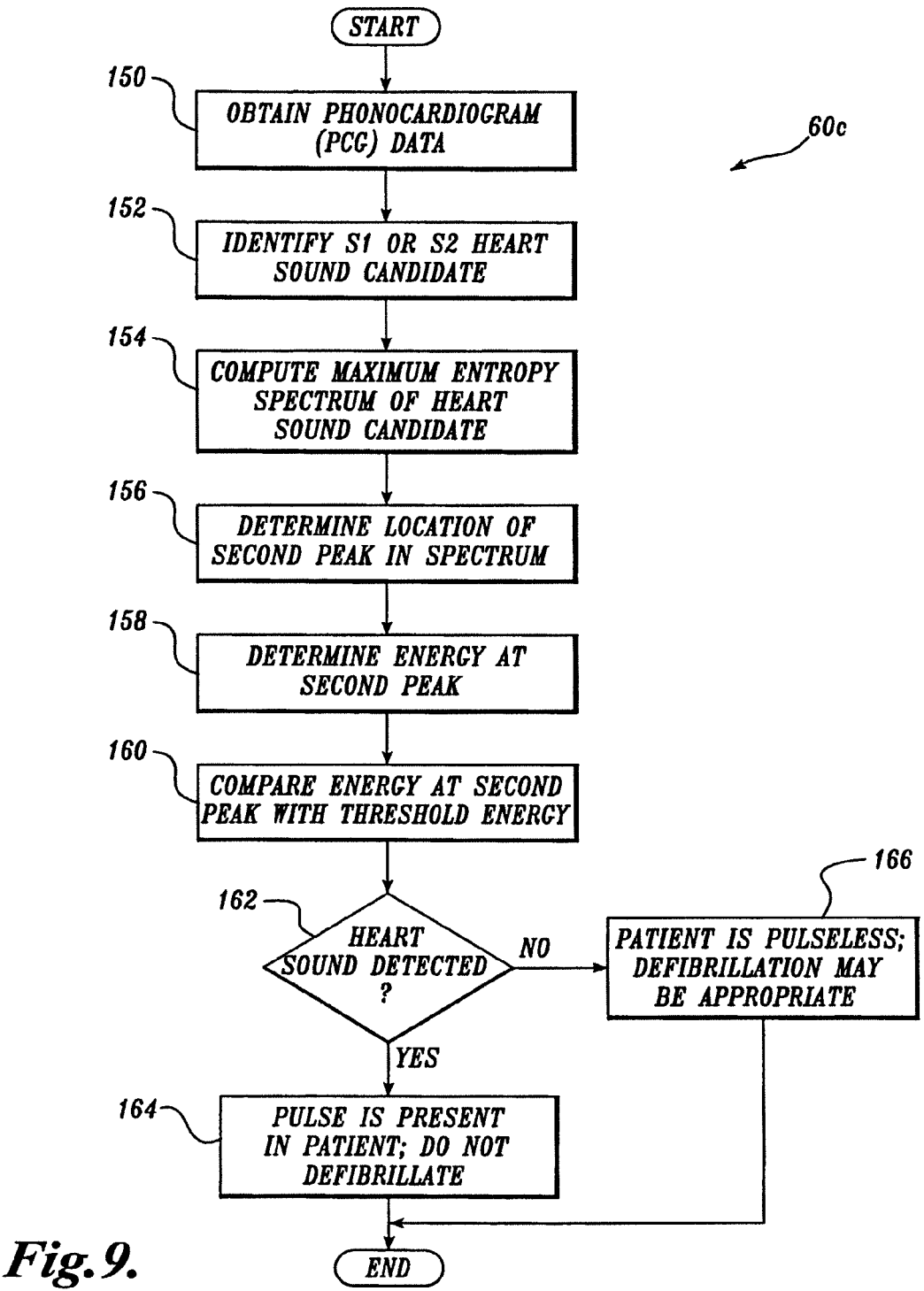
FIG. 9 is a flow diagram illustrating another pulse detection process performed by a defibrillator as shown in FIG. 2, in which a spectral peak energy analysis is performed.

FIG. 9 illustrates another pulse detection process 60*c* that also uses an MEM spectrum as calculated in block 104 of the detection process 60*b*. Instead of analyzing the frequency location of the second peak in the MEM spectrum, as performed in the process 60*b*, the process 60*c* analyzes the energy value of the second peak in the MEM spectrum.

The detection process 60*c* begins at block 150 by obtaining PCG data from the patient in a manner as discussed earlier with respect to block 70 (FIG. 4). The PCG data is analyzed in block 152 to identify PCG data corresponding to the time when a heart sound S1 or S2 likely occurred. The analysis performed in block 152 may include an energy comparison process or ECG analysis as described earlier with respect to block 102 of pulse detection process 60*b* (FIG. 6). An MEM spectrum of the heart sound candidate is then computed in block 154 in a manner as discussed earlier with respect to block 104 (FIG. 6). Also, as noted before, the energy spectrum calculation process may be run continuously.

In block 156, the pulse detection process 60*c* evaluates the energy values in the MEM spectrum to locate the second peak value in the spectrum. The energy value of the second peak, determined in a block 158, is used as a feature indicative of the presence of a heart sound, and is compared in block 160 with a predetermined threshold energy to decide whether a heart sound was detected. If the energy value of the second peak exceeds the threshold energy, the pulse detection process 60*c* determines in decision block 162 that a heart sound was detected.

If, in decision block 162, a heart sound was detected, the pulse detection process 60*c* determines in block 164 that A cardiac pulse is present in the patient. In that circumstance, the detection process 60*c* may advise against providing defibrillation therapy to the patient. The detection process may also advise to check patient breathing. On the other hand, if a heart sound was not detected in decision block 162, the pulse detection process 60*c* determines in block 166 that the patient is pulseless and advises that defibrillation therapy may be appropriate for the patient. In other embodiments, the detection process may advise the application of chest compressions or CPR in addition to or in place of advising defibrillation therapy for pulseless patients. An analysis of ECG data, as noted earlier, may be used to determine the applicability of defibrillation therapy.

FIGS. 8A and 8C illustrate one example of the processing performed by the pulse detection process 600. As discussed earlier, FIG. 8A illustrates a PCG waveform 140 of raw PCG data obtained from a patient from which an MEM spectrum is computed for a number of instances in time. For each instance in time, the energy value of the second peak in the MEM spectrum is identified, as depicted by the circles in FIG. 8C.

In FIG. 8C, the circles enclosing an "x" are the MEM spectra with a second peak having an energy value above a selected threshold energy, e.g., 0 dB. While a threshold value 0 dB is used in this specific example, other embodiments of the invention may use different threshold values to attain a desired sensitivity and specificity. The circles with an "x" in FIG. 8C generally correspond in time with the heart sounds evident in the PCG waveform 140 shown in FIG. 8A. Thus, for each circled "x," the pulse detection process 60*c* decides that a heart sound, and hence a cardiac pulse, is present in the patient.

On occasion, it is possible that noise in the PCG data may cause a false detection of a heart sound when using one of the detection processes 60*a*, 60*b*, or 60*c* described above. See, e.g., the two circled x's in FIGS. 8B and 8C immediately following the time reference of 0.6 seconds, which do not appear to correspond with heart sounds evident in FIG. 8A. If the signal-to-noise ratio of the PCG data obtained from the patient is not high enough to avoid such false detection of a heart sound, the detection processes 60*a*, 60*b*, and 60*c* of the pulse detection process may be combined in one or more ways to produce a pulse detection process with improved specificity. For example, FIG. 10 illustrates a detection process 60*d* that combines features of the detection processes 60*a*, 60*b*, and 60*c*.

Figure 10:
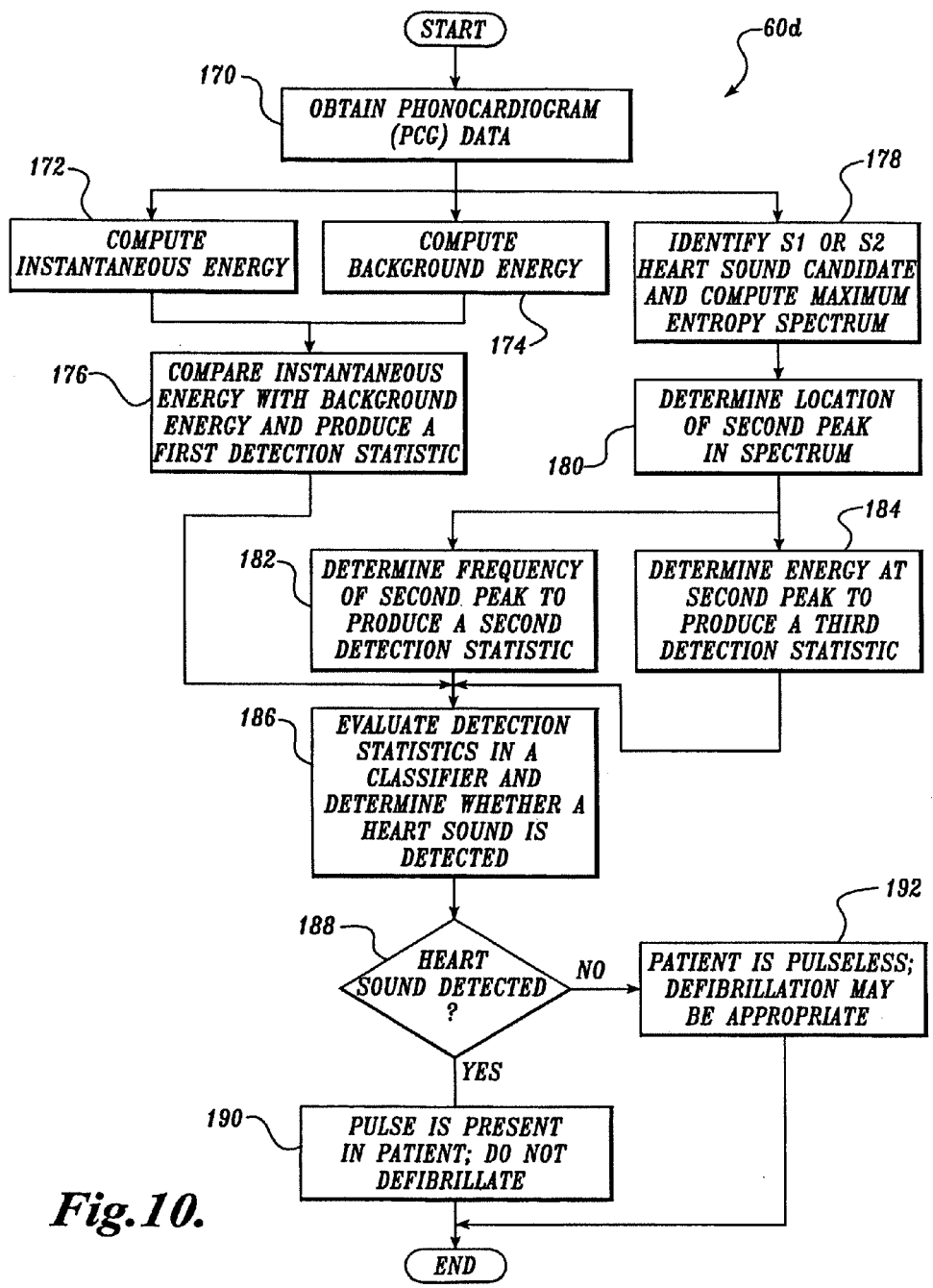
FIG. 10 is a flow diagram illustrating yet another pulse detection process performed by a defibrillator as shown in FIG. 2 that incorporates features of the pulse detection processes shown in FIGS. 4, 6 and 9.

In FIG. 10, the pulse detection process 60*d* begins at block 170 by obtaining PCG data from a patient, e.g., in a manner as described earlier with respect to block 70 of pulse detection process 60*a* (FIG. 4). After the PCG data is obtained, estimates of the instantaneous energy and the background energy in the PCG data are computed in blocks 172 and 174, e.g., in a manner as described earlier with respect to blocks 72 and 74. The estimated instantaneous and background energy values are then compared in a block 176, e.g., as described earlier with respect to block 76, to produce a first detection statistic, or feature, indicative of the presence of a heart sound. The first detection statistic produced in block 176 is provided to a multidimensional classifier in block 186 that evaluates detection statistics to determine whether a heart sound was present. Of course, those having ordinary skill in the art will recognize that the instantaneous and background energies computed in blocks 172 and 174 may also be directly provided as separate detection statistics to a multidimensional classifier in block 186 for joint classification with any other detection statistics provided to the classifier (i.e., eliminating the comparison performed in block 176).

The PCG data obtained in block 170 is also used in identifying a heart sound candidate and computing an MEM spectrum in block 178, in a manner as described earlier with respect to blocks 102 and 104 of pulse detection process 60*b* (FIG. 6). Once the MEM spectrum is computed, the pulse detection process 60*d* determines in block 180 the location of the second peak in the MEM spectrum.

The frequency of the second peak is determined in a block 182 and provided as a second detection statistic, or feature, to the classifier in block 186. Alternatively, the second detection statistic may be produced by comparing the frequency of the second peak with a threshold frequency, e.g., in a manner as described earlier with respect to block 108 (FIG. 6), to produce the second detection statistic.

In block 184, the pulse detection process 60*d* also determines the energy value at the second peak and provides the energy value as a third detection statistic, or feature, to the classifier in block 186. The second peak energy may alternatively be compared with a threshold energy, e.g., in a manner as described earlier with respect to block 160 (FIG. 9), to produce the third detection statistic.

The classifier in block 186 jointly classifies the first, second, and third detection statistics using a multidimensional classifier to determine whether a heart sound, and hence a pulse, is present in the patient. Techniques for constructing multidimensional classifiers are well-known in the art. For an expanded description of classifiers suitable for use in the present invention, see, e.g., R. Duda and P. Hart, Pattern Classification and Scene Analysis, published by John Wiley & Sons, New York, and incorporated herein by reference.

The classifier in block 186 may also use a voting scheme to determine whether a pulse is present in the patient. For example, if any of the first, second, or third detection statistics indicates the detection of a heart sound (i.e., the instantaneous energy exceeded the background energy by a threshold value, the frequency of the second peak was equal to or less than a threshold frequency, or the energy of the second peak exceeded a threshold energy), the classifier may determine that a pulse is present in the patient. Alternatively, the classifier in block 186 may determine that a pulse is present by finding that a combination of the first, second, and third detection statistics indicates the presence of a heart sound (e.g., a positive indication from the first detection statistic combined with a positive indication from the second or third detection statistics, etc.). The classifier in block 186 may also weight the first, second, or third detection statistics to emphasize one detection statistic over another in deciding whether a heart sound was detected.

If, in decision block 188, a heart sound was detected, the pulse detection process 60*d* determines in block 190 that a pulse is present in the patient and may advise the operator of the defibrillator to not defibrillate the patient. The detection process may also advise to not perform CPR, in connection with or in place of any defibrillation advice. Otherwise, if a heart sound was not detected in decision block 188, the pulse detection process 60*d* determines in block 192 that the patient is pulseless and that CPR/chest compressions and/or defibrillation therapy may be appropriate. An analysis of ECG data, as described earlier in reference to U.S. Pat. No. 4,610,254, may be used to determine if defibrillation therapy is appropriate.

An analysis of ECG data may also be combined with an analysis of PCG data to determine the presence of a cardiac pulse in the patient. In one aspect, detecting a QRS complex, or other ventricular complex, in the ECG data in time relation to the occurrence of a heart sound occurs may serve to confirm the detection of the heart sound. In another aspect, detecting a QRS complex or other ventricular complex in the ECG data may be used to identify PCG data for use in the heart sound detection process, since a heart sound is expected to occur in time proximity to the occurrence of a ventricular complex if a cardiac pulse is present in the patient. This aspect of the invention is helpful in identifying a heart sound candidate in the PCG data. It is also helpful in identifying whether the patient is in a state of pulseless electrical activity. If a ventricular complex is found in the ECG data and a heart sound does not occur within an expected time period thereafter, the patient may be considered in a state of pulseless electrical activity (PEA) which may be reported to the operator of the device. The operator may also be prompted to deliver PEA-specific therapy, as discussed herein.

While the pulse detection processes described thus far use an analysis of PCG data to determine the presence of a cardiac pulse, the pulse detection processes may analyze other physiological signals sensed in the patient for features indicative of the presence of a cardiac pulse. For instance; variations in the patient's transthoracic impedance may be associated with the discharge of blood from the heart. By monitoring characteristic variations in the patient's transthoracic impedance, the pulse detection process may monitor the patient's cardiac output, and hence determine the presence of a cardiac pulse.

Another physiological signal for use with the present invention may be obtained from a piezoelectric sensor, e.g., piezo film, placed on the surface of the patient's body. Vibrations in the chest wall caused by the patient's heart cause the piezo film to produce corresponding electric signals. The pulse detection processes of the present invention may analyze the electric signals to determine whether a cardiac pulse is present. Additional detail regarding piezoelectric sensors and pulse detection processes that use piezoelectric signal data is provided in the copending U.S. patent application titled APPARATUS, SOFTWARE, AND METHODS FOR CARDIAC PULSE DETECTION USING A PIEZOELECTRIC SENSOR, filed concurrently herewith under Ser. No. 10/229,321, and expressly incorporated by reference herein.

Another physiological signal that could be used in the present invention is obtained from one or more accelerometers placed on the patient. Vibrations in the patient from the patient's heart cause the accelerometer to output one or more electric signals, depending on the sensed axes of the accelerometers. These signals may be analyzed for one or more features indicative of a cardiac pulse. Additional detail regarding accelerometers and pulse detection processes using accelerometer signal data is provided in the co-pending U.S. Patent Application Publication No. US2004/0039420 entitled APPARATUS, SOFTWARE, AND METHODS FOR CARDIAC PULSE DETECTION USING ACCELEROMETER DATA, which is expressly incorporated herein by reference.

Yet another physiological signal that could be used in the invention is derived from photodetection (e.g., a pulse oximetry signal). Pulse oximetry uses light transmitted through the patient's skin to evaluate the oxygenation of the patient's blood. The presence of a cardiac pulse is reflected in the pulse oximetry signal. Apparatus and techniques for obtaining a pulse oximetry signal are well known in the art. One suitable system includes a sensor with a red LED, a near-infrared LED, and a photodetector diode. The sensor is configured to place the LEDs and photodetector diode directly on the skin of the patient, typically on a digit (finger or toe) or earlobe. Other places on the patient may also be suitable, including the forehead or the chest. The LEDs emit light at different frequencies, which light is diffused through the vascular bed of the patient's skin and received by the photodetector diode. The resulting pulse oximetry signal may then be analyzed according to the present invention for one or more features indicative of a cardiac pulse. Other simpler versions of a light-based pulse detection system may be used, including a version with a single light source of one or more frequencies. The absorption or reflectance of the light is modulated by the pulsatile arterial blood volume and detected using a photodetector device. One example is the Peripheral Pulse Sensor device marketed by Physio-Control in the 1970's.

A $CO_2$ waveform signal obtained from a standard capnography system is another physiological signal that could be used in the present invention. The $CO_2$ waveform is known to be affected by "cardiogenic oscillations" which are oscillations in the capnogram associated with the beating of the heart against the lungs. The capnogram may therefore be analyzed in the present invention to determine the presence of a cardiac pulse in the patient, particularly when the analysis identifies the presence of cardiac oscillations. See e.g., J. S. Gravenstein et al., Gas Monitoring in Clinical Practice, 2nd edition, Butterworth-Heinemann pp. 23-42 (1995), incorporated herein by reference.

Still another physiological signal that could be used in the present invention is a Doppler probe signal, preferably obtained from a standard continuous waveform (CW) Doppler system. A Doppler probe is attached to the patient and detects mechanical cardiac activity by sensing frequency shifts known as Doppler shifts. In accordance with the present invention, a CW Doppler probe detects Doppler shifts associated with cardiac movement and the morphology of the Doppler shifts is analyzed to determine if a pulse is present in the patient. See e.g., L. A. Geddes et al., Principles of Applied Biomedical Instrumentation, 3rd edition, John Wiley and Sons, Inc., pp. 184-209 (1989), incorporated herein by reference.

Although analysis of impedance signal data is discussed below as a way of describing further embodiments of the present invention, those of ordinary skill in the art will appreciate that the pulse detection processes of the present invention may use any physiological signal or combination of different physiological signals that reveal the presence of a cardiac pulse. These signals include, without limitation, piezoelectric. signals, accelerometer signals, pulse oximetry signals, $CO_2$ waveform signals, and Doppler probe signals as indicated above, as well as PCG signals, ECG signals, and impedance signals.

Figure 11:
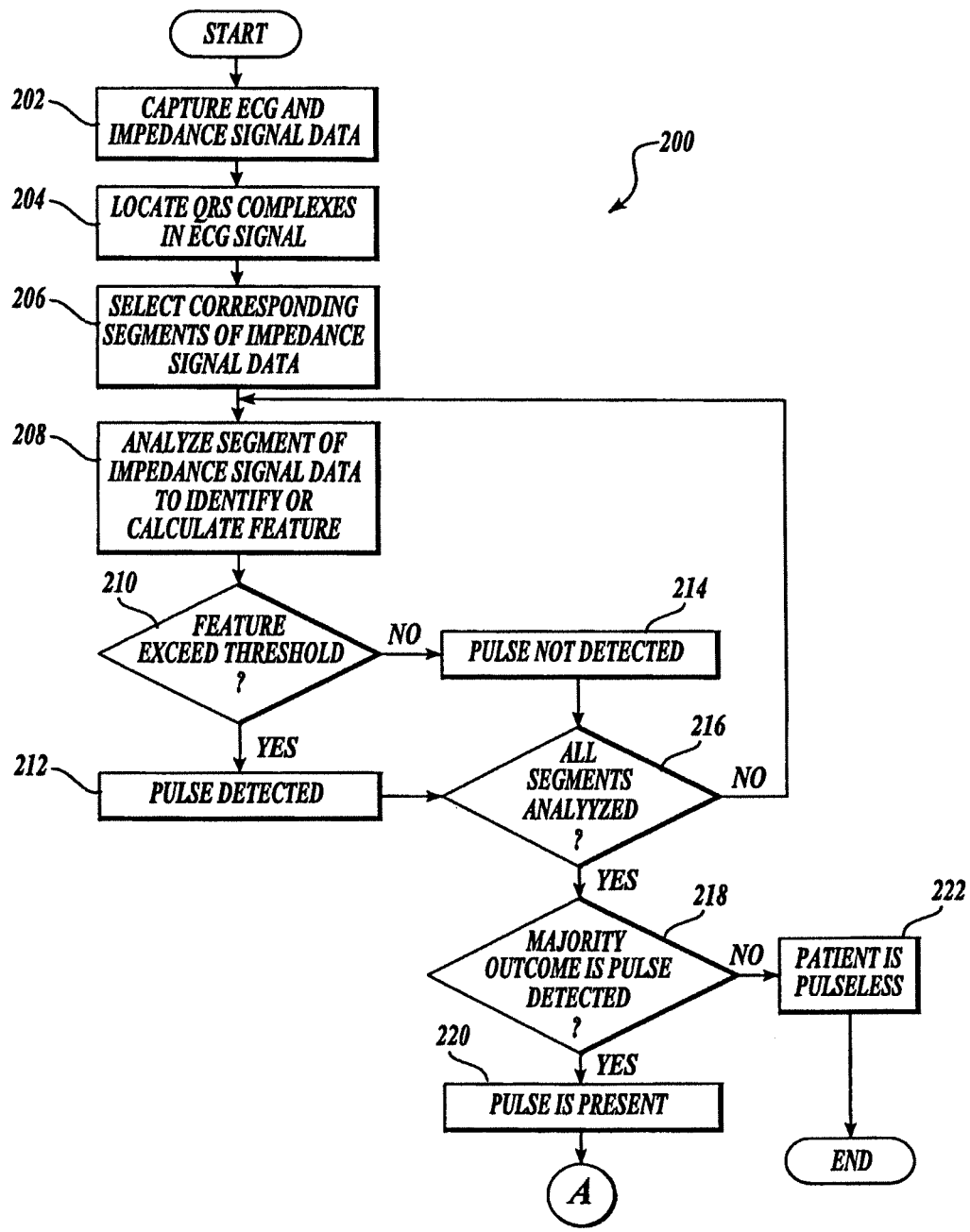
FIG. 11 is a flow diagram of a pulse detection process performed by a defibrillator as shown in FIG. 2, in which an analysis of impedance signal data is performed.

FIG. 11 illustrates a pulse detection process 200 that uses an analysis of impedance signal data to determine the presence of a pulse in a patient. Preferably, the impedance signal data selected for analysis is obtained during time intervals associated with ventricular complexes in the patient's ECG.

Beginning in block 202, the pulse detection process 200 captures both ECG and impedance signal data, synchronized in time, for a predetermined time interval (e.g., 10 seconds). Preferably, persons around the patient are advised to not touch the patient during this time interval (e.g., the device could report "Analyzing now . . . Stand clear"). Alternatively, the ECG and impedance capturing step may continue until the first or a specified number of ventricular complexes, such as QRS complexes, in the ECG have been identified, or in the event of asystole or a low heart rate, a predetermined maximum period of time (e.g., 10 seconds) has passed.

In block 204, the pulse detection process 200 locates QRS complexes in the captured ECG signal. Identification of QRS complexes can be done using methods published in the literature and well-known to those skilled in the art of ECG signal processing. For example see, Watanabe K., et al., "Computer Analysis of the Exercise ECG: A Review," Prog Cardiovasc Dis 22: 423-446, 1980.

In block 206, for each time that a QRS complex was identified in the ECG signal, a segment of filtered impedance signal data obtained from the captured impedance data is selected. In one embodiment of the invention, the time window of each segment of impedance data is approximately 600 milliseconds in length, and commences in time prior to the end of the identified QRS complex. If no QRS complexes were identified in the captured ECG signal in block 204 (as would happen for example, during asystole), no segments of impedance data are selected in block 206.

In block 208, one or more measurements are made on a segment of impedance signal data selected in block 204 to identify or calculate a feature indicative of a cardiac pulse. Non-limiting examples of the measurements may include one or more of the following temporal parameters:

(1) peak-to-peak amplitude of the impedance signal in the segment (measured in milliohms);

(2) peak-peak amplitude of the first derivative of the impedance signal in the segment (measured in milliohms per second);

(3) energy of the impedance signal in the segment (preferably calculated by squaring and summing each of the impedance data values in the segment); or (4) a pattern matching statistic.

The previously described instantaneous/background energy methods, as well as the spectral methods described herein, could be used in block 208 as well to identify or calculate a feature indicative of a cardiac pulse.

As to pattern matching, the segment of impedance signal data is compared with one or more previously identified impedance signal patterns known to predict the presence of a pulse. The comparison produces a pattern match statistic. Generally, in this context, the greater the value of the pattern match statistic, the closer the patient's impedance signal matches a pattern impedance signal that predicts the presence of a pulse. Other candidate measurements will be apparent to those skilled in the art, and may be used instead of, or in addition to, the aforementioned measurements. A measurement resulting from the analysis in block 208 constitutes a feature of the impedance signal data that may be indicative of the presence of a pulse.

In decision block 210, the one or more features from block 208 are evaluated to determine the presence of a cardiac pulse in the patient. The embodiment shown in FIG. 11 compares the one or more features to predetermined thresholds to determine whether or not a pulse is detected. For example, an impedance peak-to-peak amplitude measurement would be consistent with the presence of a pulse if the measurement exceeded a certain threshold (e.g., 50 milliohms). Similarly, an impedance energy measurement would be consistent with a pulse if its magnitude exceeded a predetermined threshold. Likewise, a pattern matching statistic would be consistent with a pulse if it exceeded a predetermined threshold. If the feature exceeded the specified threshold, the pulse detection process determines that a pulse was detected, as indicated at block 212. If the feature did not exceed the specified threshold, a pulse was not detected, as indicated at block 214. If no segments of impedance signal data were selected in block 206 (i.e., no QRS complexes were located in block 202 in the captured ECG), the pulse detection process 200 would determine that a pulse was not detected, as indicated at block 214.

The embodiment shown in FIG. 11 uses thresholding in block 210 to determine whether a pulse was detected. However, those skilled in the art will recognize other forms of classification that may suitably be used in the invention. For example, multidimensional classifiers may be used in decision block 210 to determine whether a pulse was detected. Separate analyses of the amplitude and energy in the impedance data segment may be performed, with the resultant outcome of each analysis constituting a detection statistic that is provided to a multidimensional classifier. The detection statistics may be weighted and compared in the classifier to determine an overall conclusion whether a pulse is present in the patient. In other embodiments, individual calculations of instantaneous and background amplitudes and/or energies may be provided as detection features for evaluation in a multidimensional classifier. Pattern match statistics may also be evaluated in the multidimensional classifier, as may other candidate measurements of the impedance signal data. Furthermore, spectral techniques can be used, such as the peak frequency or energy techniques described previously. Techniques for constructing multidimensional classifiers are known in the art. See, e.g., R. Duda and P. Hart, Pattern Classification and Scene Analysis, referenced earlier and incorporated herein by reference.

After determining whether a pulse was detected (block 212) or not detected (block 214), the pulse detection process 200 determines whether all of the segments of impedance signal data selected in block 206 have been analyzed. If not, the analysis and decision process of blocks 208, 210, 212, and 214 is preferably repeated for a new impedance data segment. This continues until all of the impedance data segments selected in block 206 have been analyzed.

It is recognized that the resulting determination (pulse detected or no pulse detected) may not be the same for each impedance data segment analyzed. An additional decision step is used to determine the overall outcome of the pulse detection process 200. As indicated at decision block 218, the pulse detection process 200 may evaluate the determinations for each impedance data segment and decide that a pulse is present in the patient if a pulse was detected in a simple majority of the impedance segments analyzed. Of course, other voting schemes may be used. If, in decision block 218, a majority is found, the pulse detection process concludes that a cardiac pulse is present in the patient, as indicated at block 220. Otherwise, the pulse detection process 200 concludes that the patient is pulseless, as indicated at block 222.

Requiring a pulse to be found in more than a simple majority of the impedance data segments would improve the specificity of the detection, but decrease the sensitivity for detecting a pulse. Conversely, requiring a pulse to be found for just one impedance segment or for less than a majority of the impedance segments would improve sensitivity for detecting a pulse but decrease specificity. If the pulse detection process 200 concludes that a pulse is present in the patient, the process 200 may optionally proceed to check the pulse rate of the patient, as illustrated in FIG. 12.

Figure 12:
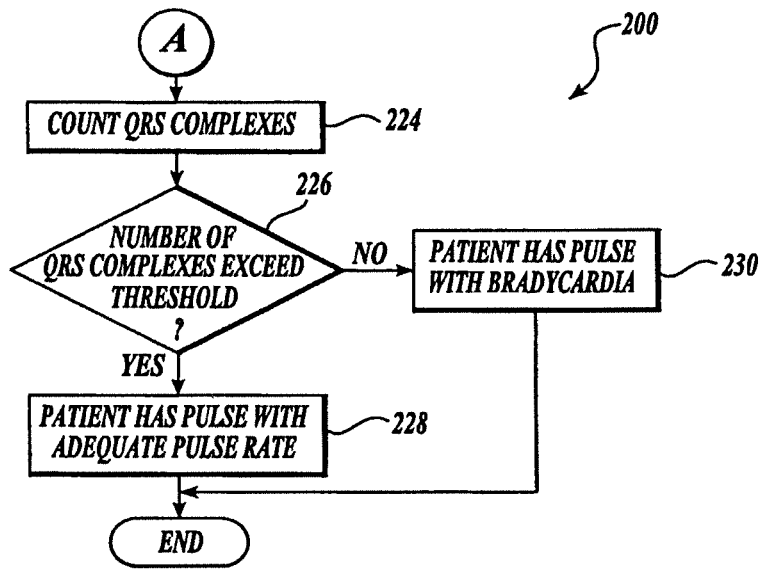
FIG. 12 is a flow diagram of a pulse rate analysis performed with the pulse detection process shown in FIG. 11.

Turning to FIG. 12, in block 224, the number of QRS complexes (located in block 204 in FIG. 11) are counted. Decision block 226 subsequently compares the number of QRS complexes to a threshold. In one exemplary embodiment, the threshold is 5, corresponding to a heart rate of approximately 30 bpm. If the number of QRS complexes is at least equal to the threshold, the pulse detection process 200 proceeds to block 228, concluding that the patient has a pulse and an adequate pulse rate. If the number of QRS complexes is less than the threshold, the pulse detection process 200 proceeds to block 230, concluding that the patient has a pulse, but also severe bradycardia. At very low heart rates, however, the blood flow may be insufficient to support life. For that reason, below a certain heart rate (e.g., 30 bpm), the patient may instead be considered pulseless.

Figure 13:
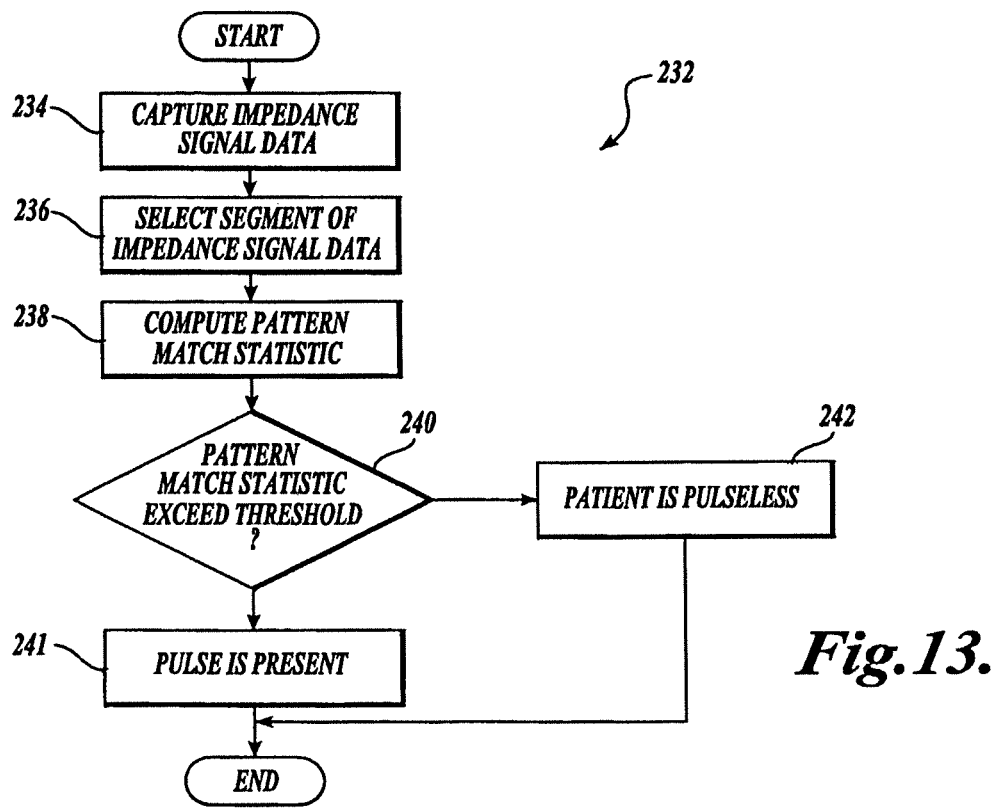
FIG. 13 is a flow diagram of another pulse detection process performed in accordance with the present invention in which an impedance signal pattern analysis is performed without an ECG signal analysis.

While the pulse detection process shown in FIG. 11 includes capturing both ECG and impedance signal data, and selecting the segments of impedance signal data based on ventricular complexes located in the ECG, other pulse detection processes may not capture or use the ECG signal. In FIG. 13, an alternative pulse detection process 232 begins by capturing only impedance signal data from the patient, as indicated at block 234. Depending on the length of the time interval in which impedance data is captured, it may be advantageous to select a segment of the impedance signal data for further analysis, as indicated at block 236. In that regard, one suitable selection process includes scanning the impedance signal data for the maximum peak and selecting a segment of data that surrounds the detected maximum peak.

For exemplary purposes, the pulse detection process 232 is shown evaluating the selected segment of impedance signal data using a pattern match analysis. However, those skilled in the art will recognize that other techniques (e.g., analysis of the amplitude or energy—temporal or spectral—in the impedance signal data, as discussed above), may be used. In block 238, the selected impedance data segment is compared with previously identified impedance signal patterns known to predict the presence of a pulse. The resulting pattern match statistic is evaluated against a threshold in decision block 240 to determine whether a pulse was detected in the patient. If the pattern match statistic exceeded the threshold, the pulse detection process 232 concludes in block 241 that a pulse was detected in the patient. Otherwise, the pulse detection process 232 concludes that the patient is pulseless, as indicated in block 242. At this point, the pulse detection process is finished. Alternatively, if a pulse was detected in the patient, the pulse detection process 232 may proceed to evaluate the patient's pulse rate in a manner described in reference to FIG. 12.

The transthoracic impedance signal can contain fluctuations due to cardiac pulses, respiration, or patient motion. To assess whether a patient has a pulse, it is desirable to suppress fluctuations in the patient's impedance that are due to causes other than cardiac pulses. Fluctuations due to noncardiac causes may contain components at frequencies similar to those of impedance fluctuations due to cardiac pulses. Consequently, bandpass filtering may not always adequately suppress fluctuations due to noncardiac causes.

Signal averaging of the impedance signal can be used to suppress fluctuations that are due to noncardiac causes. Signal averaging makes advantageous use of the fact that impedance fluctuations due to cardiac pulses are generally synchronized to ventricular complexes in the ECG signal, whereas other impedance fluctuations are asynchronous to ventricular complexes. Pulse detection may be more accurately accomplished using an averaged impedance signal.

A preferred method for signal averaging of the impedance signal first stores the continuous ECG and transthoracic impedance signals, synchronized in time, for a predetermined time interval (e.g., ten seconds). The locations of the QRS complexes (if any) in the stored ECG signal are determined. Using true mathematical correlation (or an alternative correlation technique such as area of difference), the QRS complexes are classified into types, where all QRS complexes of the same type have high correlation with the first occurring QRS complex of that type. The dominant QRS type is selected as the type containing the most members, with a preference for the narrowest QRS type when a two or more types tie for most members. Using the first QRS of the dominant type as a reference complex, the second QRS complex of the same type is shifted in time until it is best aligned with the reference complex (i.e., it achieves a maximum correlation value). The corresponding impedance signal is also shifted in time to stay synchronized with the time-shifted QRS complex. When the second QRS complex is optimally aligned with the reference complex, the two QRS complexes are averaged together. Their corresponding impedance signals, over a time period from about the start of the QRS complex to about 600 milliseconds after the end of the QRS complex, are also averaged together. The averaged QRS complex is then used as a new reference complex and the process of averaging both the QRS complexes and the corresponding impedance data is repeated with the remaining QRS complexes of the dominant type.

Preferably, during the subsequent averaging of the QRS complexes and impedance segments, the new QRS complex and impedance segment carry a weight of one and the previous averaged QRS complex and impedance segment carry a weight equal to the number of QRS complexes that have been included in the averaged QRS complex. When all of the QRS complexes of the dominant type have been processed as described above, the averaged impedance segment is evaluated using one or more of the techniques previously described (e.g., amplitude, energy, pattern matching) to determine whether the patient has a pulse.

Averaging of the signal data (be it PCG data, impedance data, etc., or combinations thereof) may also be accomplished without evaluating ECG data. For example, segments of impedance data may be analyzed and classified into types where segments of the same type have a high correlation.

Impedance data of a dominant type, for example, may then be averaged and evaluated as previously described (using amplitude, energy, pattern matching, etc.) to determine whether the patient has a pulse.

During severe bradycardia, there will be few QRS complexes in a 10-second period and signal averaging of the transthoracic impedance signal will not be as effective as when the heart rate is higher. However, at very low heart rates, there is unlikely to be enough blood flow to support life. For that reason, below a certain heart rate (e.g., 30 bpm), the patient may be considered pulseless.

Figure 14:
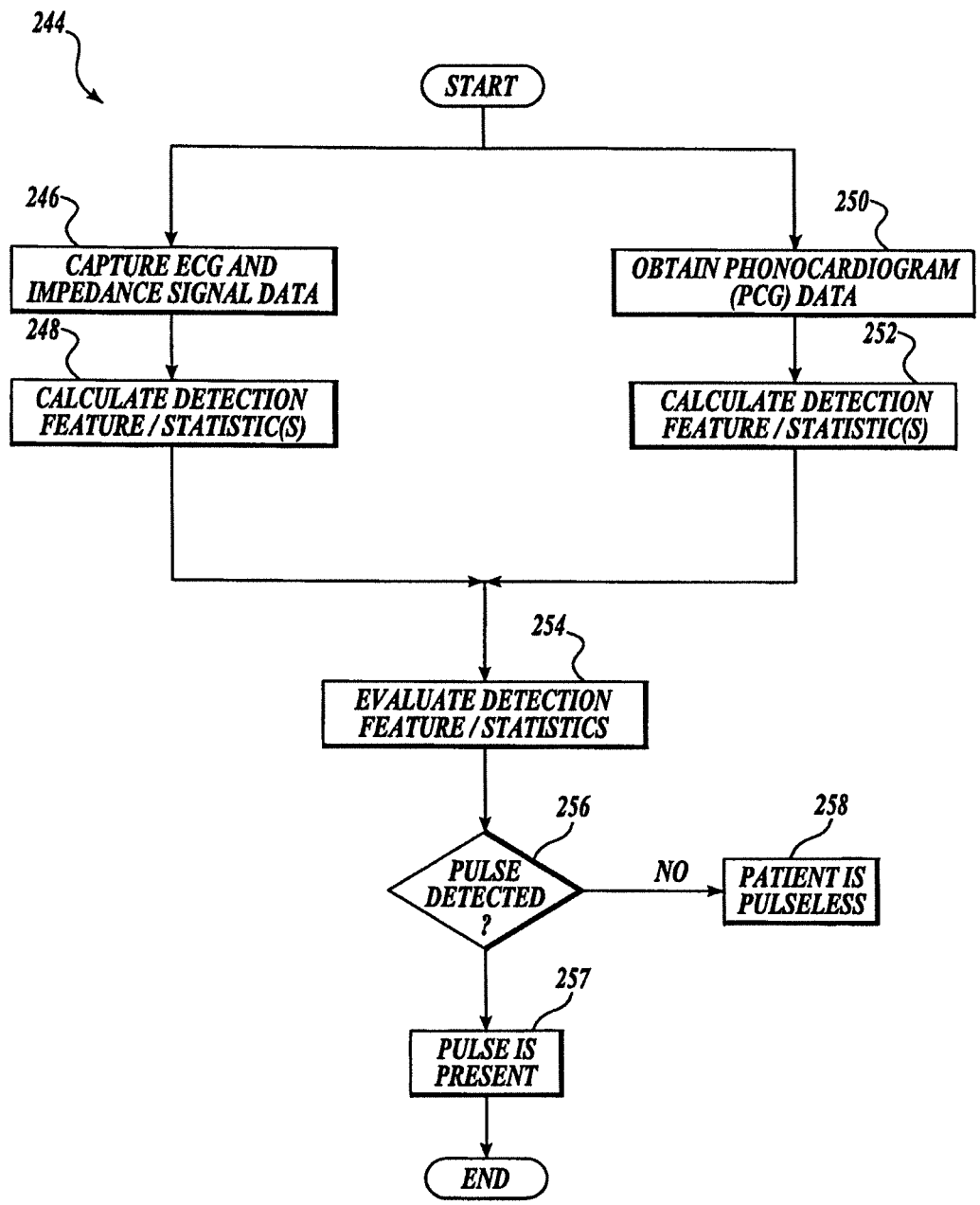
FIG. 14 is a flow diagram of a pulse detection process of the present invention that analyzes multiple physiological signals, in this case impedance and, heart sound signals, to determine the presence of a cardiac pulse.

While the pulse detection processes described thus far separately use a PCG signal or impedance signal to determine the presence of a pulse, it is further within the scope of the present invention to combine multiple physiological signals into a pulse detection process. For example, the pulse detection process 244 depicted in FIG. 14 illustrates an exemplary process in which PCG data and impedance signal data are used in combination to determine the presence of a pulse. In block 246, the pulse detection process 244 captures impedance signal data from the patient, and in this example, captures ECG data as well. This capturing process may be performed in a manner similar to that described with respect to block 202 in FIG. 11. In block 248, the pulse detection process 244 calculates one or more detection features or statistics. For example, the detection process 244 may undertake actions similar to that described with respect to blocks 204, 206, 208, and 210 to produce an impedance-based detection statistic reflecting a preliminary determination whether a pulse has been detected.

At the same time as, or before or after, the impedance signal analysis in blocks 246 and 248, the pulse detection process 244 also undertakes a PCG signal analysis. In that respect, in block 250, the detection process 244 obtains phonocardiogram (PCG) data from the patient as described earlier in block 70 of FIG. 4. The PCG data is used to calculate one or more detection features or statistics in block 252. For example, the detection process 244 may undertake actions as described above with regard to any or all of the pulse detection processes 60a, 60b, and/or 60c. As noted earlier, FIG. 10 illustrates a PCG-based detection process 60d that combines the detection processes 60a, 60b, and 60c. As shown in FIG. 10, each of the pulse detection processes produces a first, second, and third detection statistic that are fed to a multidimensional classifier. In regard to FIG. 14, the detection statistics from the impedance-based and PCG-based detection processes are provided to a classifier for evaluation, as shown in block 254. The classifier in block 254 may be a multidimensional classifier as described above with respect to block 186 (FIG. 10). As noted earlier, the reference Pattern Classification and Scene Analysis by R. Duda and P. Hart, describes techniques for constructing suitable multidimensional classifiers. Additionally, techniques for multidimensional classifiers are discussed in U.S. Pat. No. 6,171,256, assigned to the assignee of the present invention and incorporated by reference herein.

The outcome of the classification performed in block 254 is provided to a decision block 256. If the detection statistics are classified as indicating the presence of a pulse, the pulse detection process 244 determines in block 257 that a cardiac pulse is present and preferably advises against providing defibrillation therapy to the patient. On the other hand, if the detection statistics are classified as not indicating the presence of a pulse, the pulse detection process 244 determines in block 258 that a cardiac pulse was not detected and may advise the delivery of defibrillation therapy.

There is no restriction as to what constitutes a detection feature/statistic for the purposes of the pulse detection process 244. A detection feature/statistic may suitably be a preliminary determination of whether a pulse is present (i.e., a binary "yes" or "no" outcome). A detection feature/statistic may also be data produced from the analyzed physiological signal. For example, a detection feature/statistic may be an amplitude, energy, or pattern match statistic as discussed earlier. The detection feature/statistic may also be an energy or frequency value in the temporal or spectral domain. A combination of two or more analyzed physiological signals may advantageously provide a more robust pulse detection process with improved detection characteristics.

Figure 15:
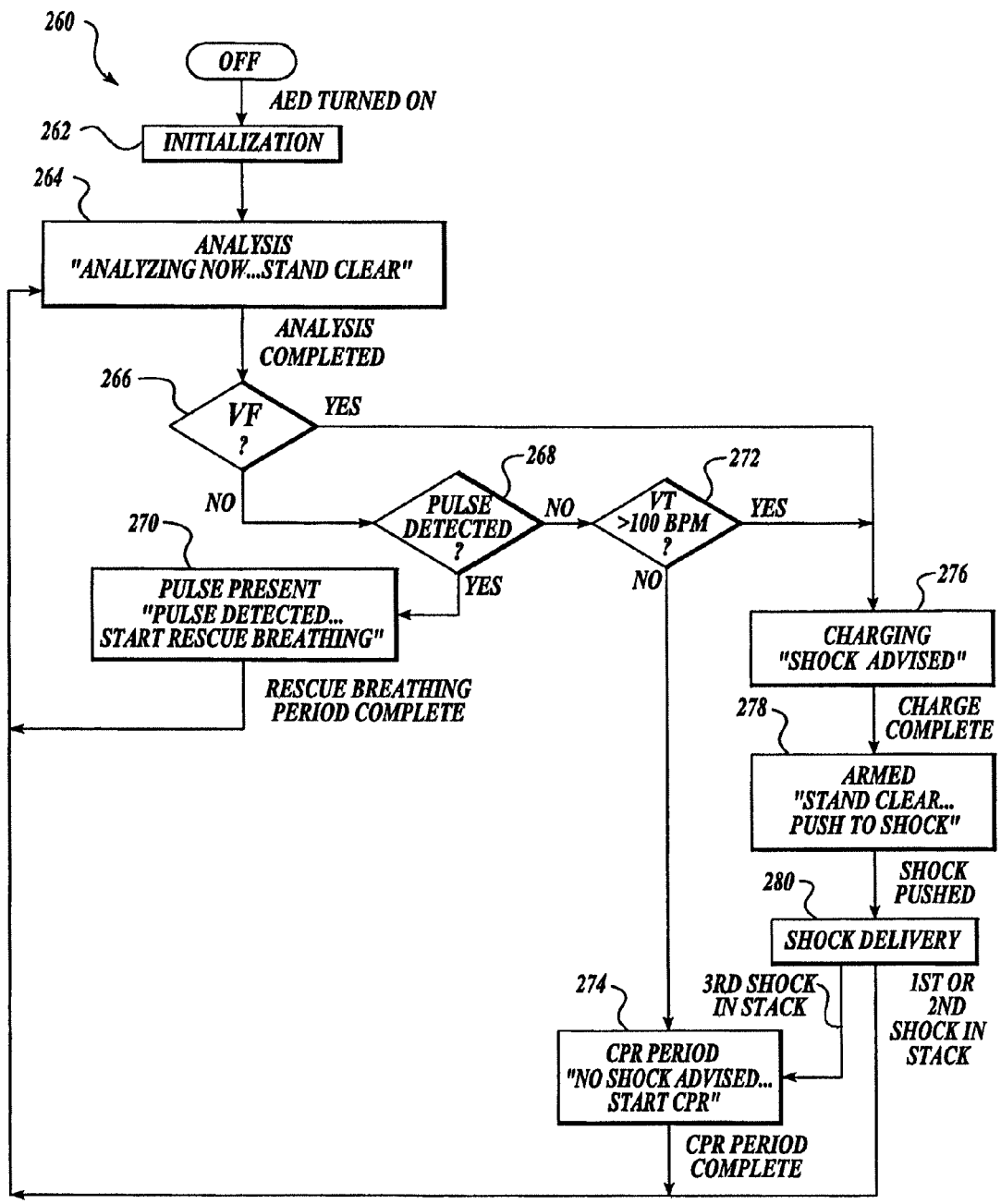
FIG. 15 is a flow diagram of a procedure implemented by a defibrillator as shown in FIG. 2 that incorporates a pulse detection process provided by the present invention.

A pulse detection process as described herein may be used as part of an overall shock advisory process in a defibrillator. The shock advisory process determines whether to recommend defibrillation or other forms of therapy for a patient. FIG. 15 illustrates a pulse detection/defibrillation process 260, preferably for use in an automated external defibrillator (AED) capable of providing a defibrillation pulse if a patient is determined to be pulseless and in ventricular fibrillation or ventricular tachycardia. The AED may also be configured to prompt the application of chest compressions or CPR as appropriate.

In the pulse detection/defibrillation process 260, an AED initializes its circuits when it is first turned on, as indicated at block 262. The defibrillation electrodes of the AED are placed on the patient. When the AED is ready for operation, the process 260 performs an analysis of the patient, as indicated at block 264, in which the AED obtains selected parameters such as impedance signal data, ECG data, and/or PCG data, from the patient. During the analysis performed in block 264, the AED preferably reports "Analyzing now . . . Stand clear" to the operator of the AED.

Using the information obtained in the patient analysis, the process 260 determines in decision block 266 whether the patient is experiencing ventricular fibrillation (VF). If VF is present in the patient, the process 260 proceeds to block 276 where the AED prepares to deliver a defibrillation pulse to the patient. In that regard, an energy storage device within the AED, such as a capacitor, is charged. At the same time, the AED reports "Shock advised" to the operator of the AED.

Once the energy storage device is charged, the process 260 proceeds to block 278 where the AED is ready to deliver the defibrillation pulse. The operator of the AED is advised "Stand clear . . . Push to shock." When the operator of the AED initiates delivery of the defibrillation pulse, the process 260 delivers the defibrillation shock to the patient, as indicated in block 280.

The AED preferably records in memory that it delivered a defibrillation pulse to the patient. If the present pulse delivery is the first or second defibrillation shock delivered to the patient, the process 260 may return to block 264 where the patient undergoes another analysis. On the other hand, if the pulse delivery was the third defibrillation pulse to be delivered to the patient, the process 260 may proceed to block 274 where the AED advises the operator to commence providing CPR therapy to the patient, e.g., by using the message "Start CPR." The "No shock advised" prompt shown in block 274 is suppressed in this instance. The AED may continue to prompt for CPR for a predetermined time period, after which the patient may again be analyzed, as indicated in block 264.

Returning to decision block 266, if VF is not detected in the patient, the process 260 proceeds to decision block 268 and determines whether a cardiac pulse is present in the patient. The pulse detection performed in block 268 may be any one or a combination of the pulse detection processes described above.

Breathing may be checked manually by the operator or automatically by the device, as discussed below in regard to block 374 of FIG. 17. If, at decision block 268, a pulse is detected in the patient and the patient is not breathing, the process 260 proceeds to block 270 and reports "Pulse detected . . . Start rescue breathing" to the operator. The process 260 may also report "Return of spontaneous circulation" if a pulse is detected in the patient any time after the delivery of a defibrillation pulse in block 280. In any event, after a predetermined time period for rescue breathing has completed, the process 260 preferably returns to block 264 to repeat an analysis of the patient.

If a cardiac pulse is not detected at decision block 268, the process 260 determines whether the patient is experiencing ventricular tachycardia (VT) with a heart rate of greater than a certain threshold, e.g., 100 beats per minute (bpm), as indicated at decision block 272. Other thresholds such as 120, 150, or 180 bpm, for example, may be used. If the determination at decision block 272 is negative, the process 260 proceeds to block 274 and advises the operator to provide CPR therapy. Again, at this point, the AED reports "No shock advised . . . Start CPR" to the operator. The prompt to provide CPR is preferably provided for a defined period of time. When the period of time for CPR is finished, the process 260 preferably returns to block 264 and performs another analysis of the patient. If the determination at decision block 272 is positive (i.e., the patient is experiencing VT with a heart rate greater than the threshold), the process 260 performs the shock sequence shown at blocks 276, 278, 280 to deliver a defibrillation pulse.

Figure 16:
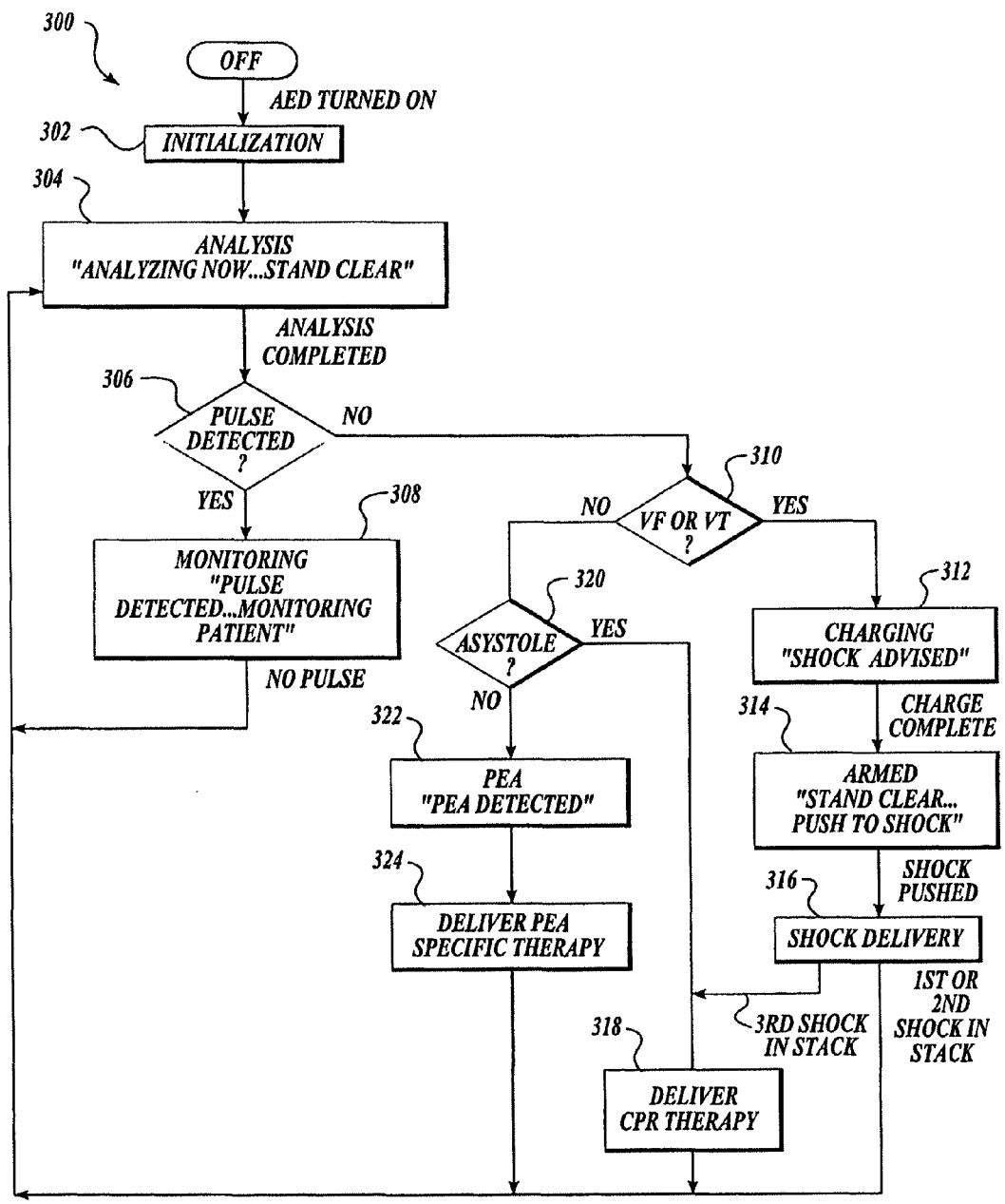
FIG. 16 is a flow diagram of another procedure implemented by a defibrillator as shown in FIG. 2 that incorporates a pulse detection process provided by the present invention.

Those having ordinary skill in defibrillation and cardiac therapy will recognize variations and additions to the process 260 within the scope of the invention. FIG. 16, for example, illustrates an alternative pulse detection/defibrillation process 300 for use in an AED. As with the process 260 in FIG. 15, the AED begins by initializing its circuits at block 302. At block 304, the AED performs an analysis of the patient in a manner similar to that described with respect to block 264 in FIG. 15. After completing the analysis of the patient, the process 300 proceeds to decision block 306 to determine whether a pulse is present in the patient. The pulse detection performed in block 306 may be, for example, any one of the pulse detection processes discussed above or a combination or variation thereof.

If a pulse is detected in the patient, the process 300 may enter a monitoring mode at block 308 in which the patient's pulse is monitored. The pulse monitoring performed at block 308 may use any one or a combination of the pulse detection processes described above. Preferably, the process 300 is configured to proceed from block 308 to block 304 after expiration of the predetermined monitoring time period. If the pulse monitoring at block 308 determines at any time that a pulse is no longer detected, the process 300 returns to block 304 to perform another analysis of the patient. The process 300 also preferably reports the change in patient condition to the operator.

If, at decision block 306, a pulse is not detected in the patient, the process 300 proceeds to decision block 310 where it determines whether the patient has a shockable cardiac rhythm (e.g., VF or VT). As referenced earlier, U.S. Pat. No. 4,610,254, incorporated herein by reference, describes a suitable method for differentiating shockable from non-shockable cardiac rhythms.

If a shockable cardiac rhythm, such as VF or VT, is detected, the process 300 proceeds to a shock delivery sequence at blocks 312, 314, and 316, which may operate in a manner similar to that described with respect to blocks 276, 278, and 280 in FIG. 15. If the pulse delivery was the third defibrillation shock delivered to the patient, the process 300 may proceed to block 318 and prompt the delivery of CPR, as discussed with block 274 in FIG. 15.

If VF or VT is not detected at decision block 310, the process 300 checks for asystole, as indicated at block 320. One suitable process for detecting asystole is described in U.S. Pat. No. 6,304,773, assigned to the assignee of the present invention and incorporated herein by reference. If asystole is detected at block 320, the process 300 proceeds to prompt the delivery of CPR, as indicated at block 318. If asystole is not detected, the process 300 determines that the patient is experiencing pulseless electrical activity (PEA), as indicated at block 322. PEA is generally defined by the presence of QRS complexes in a patient and the lack of a detectable pulse, combined with no detection of VT or VF. Detection of PEA in block 322 is achieved by ruling out the presence of a pulse (block 306), detecting no VF or VT (block 310), and detecting no asystole (block 320). Alternatively, if the ECG signal is monitored for QRS complexes (e.g., as shown at block 202 in FIG. 11), the process 300 may conclude the patient is in a state of PEA if it repeatedly observes QRS complexes without detection of a cardiac pulse associated therewith. If a PEA condition is detected, the process 300 proceeds to block 324 and prompts the operator to deliver PEA-specific therapy to the patient. One suitable method of treating PEA is described in U.S. Pat. No. 6,298,267, incorporated by reference herein. The process 300 may prompt other therapies as well, provided they are designed for a PEA condition. After a PEA-specific therapy has been delivered to the patient, possibly for a predetermined period of time, the process 300 returns to block 304 to repeat the analysis of the patient.

Figure 17:
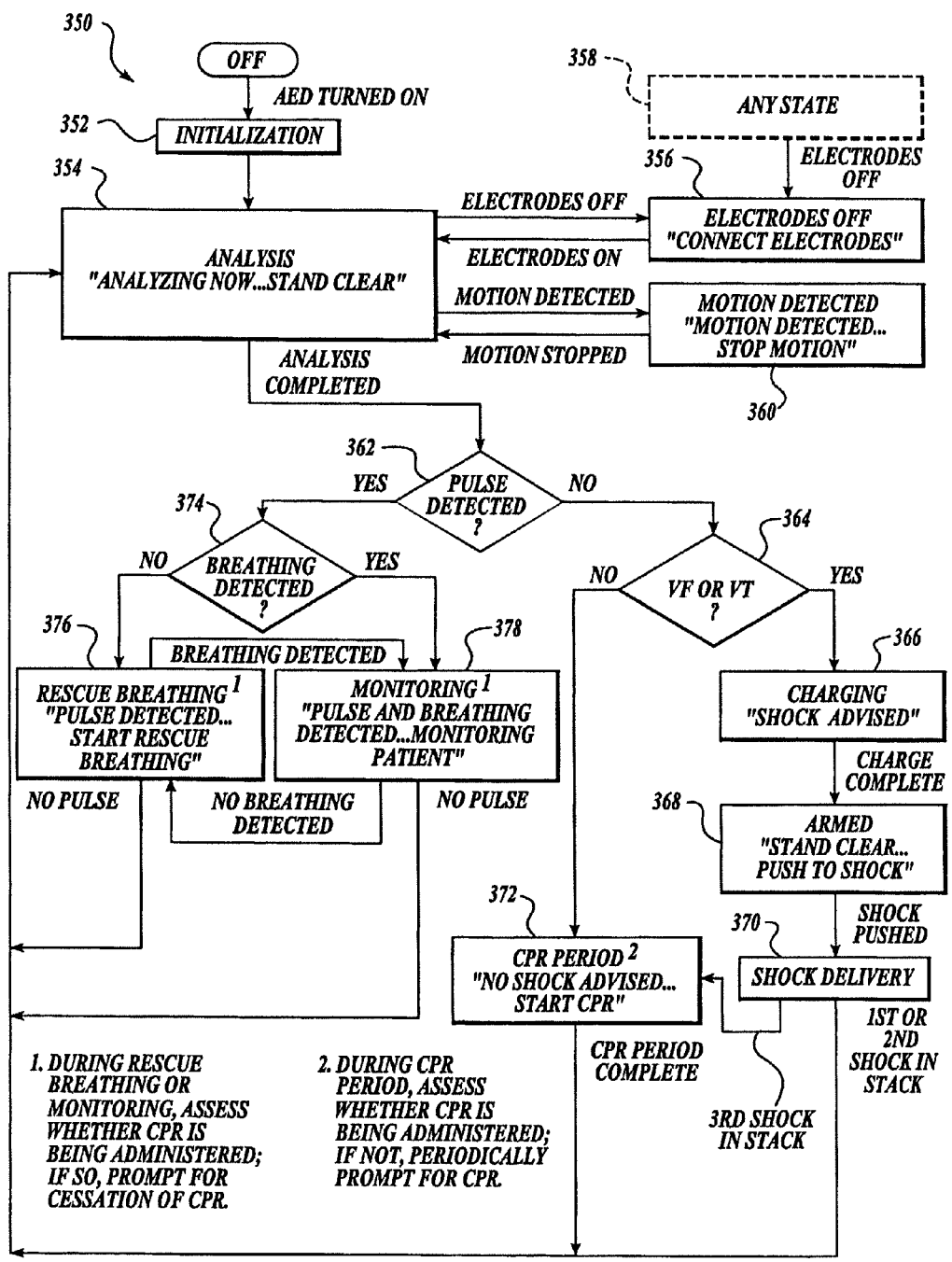
FIG. 17 is a flow diagram of still another procedure implemented by a defibrillator as shown in FIG. 2 that incorporates a pulse detection process provided by the present invention.

FIG. 17 illustrates yet another pulse detection/defibrillation process 350 that may be used in an AED. At block 352, after the AED has been turned on, the AED initializes its circuits. The defibrillation electrodes are also placed on the patient. The AED is then ready to analyze the patient, as indicated at block 354. This analysis may be performed in a manner similar to that described with respect to block 264 in FIG. 15.

If at any point the AED determines that the defibrillation electrodes are not connected to the AED, the process 350 jumps to block 356 where the AED instructs the operator to "Connect electrodes." When the AED senses that the electrodes are connected, the process 350 returns to the analysis in block 354. Likewise, if the AED finds itself in any other state where the electrodes are not connected, as represented by block 358, the process 350 jumps to block 356 where it instructs the operator to connect the electrodes.

Furthermore, during the analysis performed in block 354, if the AED detects motion on the part of the patient, the process 350 proceeds to block 360 where the AED reports to the operator of the AED "Motion detected . . . Stop motion." If the patient is moved during the analysis process 354, the data obtained during the analysis is more likely to be affected by noise and other signal contaminants. Motion of the patient may be detected in the impedance signal data collected by the present invention. A suitable method for detecting motion of the patient is described in U.S. Pat. No. 4,610,254, referenced earlier and incorporated by reference herein. The AED evaluates the impedance measured between the defibrillation electrodes placed on the patient. As noted earlier, noise and signal components resulting from patient motion cause fluctuations in the impedance signal, generally in a frequency range of 1-3 Hz. If the measured impedance fluctuates outside of a predetermined range, the AED determines that the patient is moving or being moved and directs the process 350 to proceed to block 360. When the motion ceases, the process 350 returns to the analysis in block 354.

The process 350 next proceeds to decision block 362 where it determines whether a pulse is detected in the patient. Again, the pulse detection processes performed in decision block 362 may be, for example, one of the pulse detection processes described above or combination or variation thereof.

If a pulse is not detected in the patient, the process 350 proceeds to decision block 364 where it determines whether the patient has a shockable cardiac rhythm (e.g., VF or VT) or a non-shockable cardiac rhythm (such as asystole and bradycardia). As. referenced earlier, one suitable method for differentiating shockable from non-shockable cardiac rhythms is disclosed in U.S. Pat. No. 4,610,254, incorporated herein by reference. If the patient's cardiac rhythm is determined to be shockable (e.g., VF or VT is found), the process 350 proceeds to blocks 366, 368, and 370 to deliver a shock to the patient. The shock delivery may be performed as described earlier with respect to blocks 276, 278, 280 in FIG. 15.

If the pulse delivery was the third defibrillation pulse to be delivered to the patient, the process 350 proceeds to block 372 where the AED advises the operator to commence providing CPR therapy to the patient. The CPR prompt may continue for a defined period of time, at which the process 350 returns to block 354 and performs another analysis of the patient.

If, at decision block 364, the patient's cardiac rhythm is determined not shockable, the process 350 preferably proceeds to block 372 and advises the operator to provide CPR therapy, as discussed above.

Returning to decision block 362, if a pulse is detected in the patient, the process 350 proceeds to decision block 374 where it determines whether the patient is breathing. In that regard, the AED may again use the impedance signal for determining whether a patient is breathing. As noted earlier, fluctuations in impedance of the patient below 1 Hz are largely indicative of a change in volume of the patient's lungs. The breathing detection at block 374 (and at blocks 376 and 378, discussed below) may monitor the impedance signal for characteristic changes that indicate patient breathing, e.g., as described in Hoffmans et al., "Respiratory Monitoring With a New Impedance Plethysmograph," Anesthesia 41: 1139-42, 1986, and incorporated by reference herein. Detection of breathing may employ a process similar to that described above for detection of a pulse (i.e., evaluating impedance amplitude, energy, or pattern), though a different bandpass filter would be used to isolate the frequency components that more closely demonstrate patient breathing. If automatic means for detecting breathing in the patient are not available, the AED may ask the operator of the AED to input information (e.g., by pressing a button) to indicate whether the patient is breathing.

If, at decision block 374, the process 350 determines that the patient is not breathing, the process 350 proceeds to a block 376 where the operator of the AED is advised to commence rescue breathing. In that regard, the AED reports to the operator "Pulse detected . . . Start rescue breathing." The AED also continues to monitor the patient's cardiac pulse and returns to block 354 if a cardiac pulse is no longer detected. If, at any point during the provision of rescue breathing, the AED detects that the patient is breathing on his own, the process 350 proceeds to block 378 where the AED monitors the patient for a continued presence of breathing and a cardiac pulse.

Returning to decision block 374, if the process 350 determines that the patient is breathing, the process 350 proceeds to block 378 where the AED monitors the pulse and breathing of the patient. In that regard, the AED reports "Pulse and breathing detected . . . Monitoring patient." If, at any time during the monitoring of the patient the process 350 determines that the patient is not breathing, the process 350 proceeds to block 376 where the operator of the AED is advised to commence rescue breathing. If a cardiac pulse is no longer detected in the patient, the process 350 proceeds from either block 376 or 378 to block 354 to commence a new analysis of the patient.

Lastly, as noted in FIG. 17, during the rescue breathing procedure in block 376 or the monitoring procedure performed in block 378, the AED may assess whether CPR is being administered to the patient. If the AED finds that CPR is being performed, the AED may prompt the operator to cease providing CPR. If, during the CPR period of block 372, the AED determines that CPR is not being administered to the patient, the AED may remind the operator to provide CPR therapy to the patient. One method for determining whether CPR is being administered is to monitor patient impedance to observe patterns of impedance fluctuation in the patient that are indicative of CPR. During CPR, repetitive chest compression typically causes repetitive fluctuations in the impedance signal.

Figure 18:
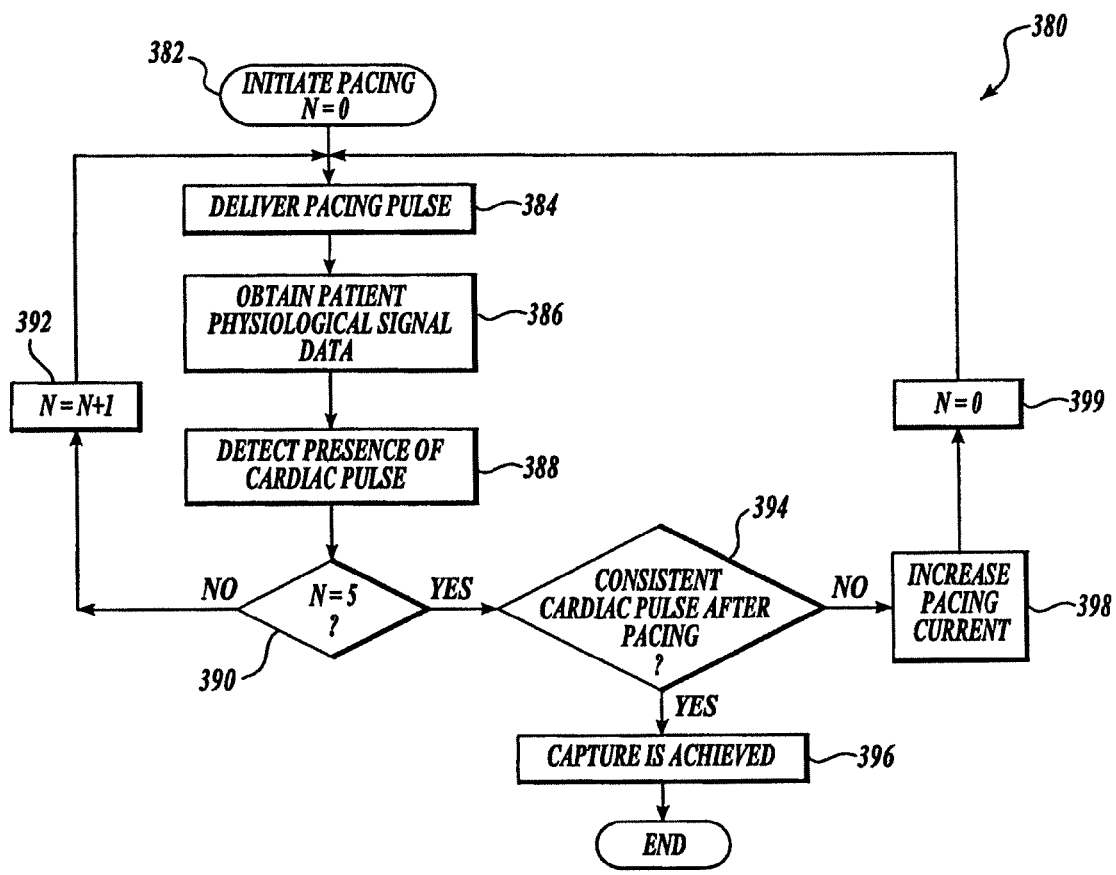
FIG. 18 is a flow diagram of an auto-capture detection process for cardiac pacing that uses a pulse detection process of the present invention.

FIG. 18 illustrates yet another application in which pulse detection according to the present invention may be used. The application described in FIG. 18 pertains to auto-capture detection in cardiac pacing.

Specifically, the auto-capture detection process 380 begins at block 382 in which pacing therapy for the patient is initiated. A counter N, described below, is set to equal 0. At block 384, a pacing pulse is delivered to the patient. Thereafter, physiological signal data is obtained from the patient, as indicated at block 386. This data may include, for example, PCG data, ECG data impedance signal data, piezoelectric signal data, accelerometer data, etc., or a combination of this data, that is capable of indicating the presence of a cardiac pulse. The patient's physiological signal data is used in block 388 to detect the presence of a cardiac pulse. The pulse detection process used in block 388 may be, for example, any one or combination or variation of the pulse detection processes discussed above.

The sequence of delivering a pacing pulse and determining the presence of a cardiac pulse in blocks 384, 386, 388 may be repeated a number of times. With respect to FIG. 18, for example, the sequence is repeated five times. At block 390, the counter N is evaluated, and if not yet equal to 5, the counter is incremented by 1 (block 392), following which the process 380 returns to deliver another pacing pulse to the patient (block 384).

If, at decision block 390, the counter N equals 5, the process 380 determines at decision block 394 whether a cardiac pulse occurred consistently after each pacing pulse. The process 380 requires that some portion or all of the pacing pulses result in a detectable cardiac pulse before pronouncing that capture has been achieved. If the presence of a cardiac pulse is determined to consistently follow the pacing pulses, the process 380 determines that capture has been achieved, as in indicated at block 396. Otherwise, the current of the pacing pulses is increased by a predetermined amount, e.g., 10 milliamperes, as indicated at block 398. At block 399, the counter N is set back to equal 0 and the process 380 returns to the pacing capture detection sequence beginning at block 384. In this manner, the pacing current is increased until capture has been achieved.

In FIG. 18, the presence of a pulse is used to determine whether the pacing stimulus has been captured by the ventricles of the patient's heart. Detection of QRS complexes in the patient's ECG may also be used as patient physiological signal data to identify pacing capture. A QRS complex will occur immediately following the pacing stimulus if capture has been achieved. If QRS complexes are not observed, the current of the pacing pulses may be increased, as discussed above, until capture has been achieved.

Figure 19:
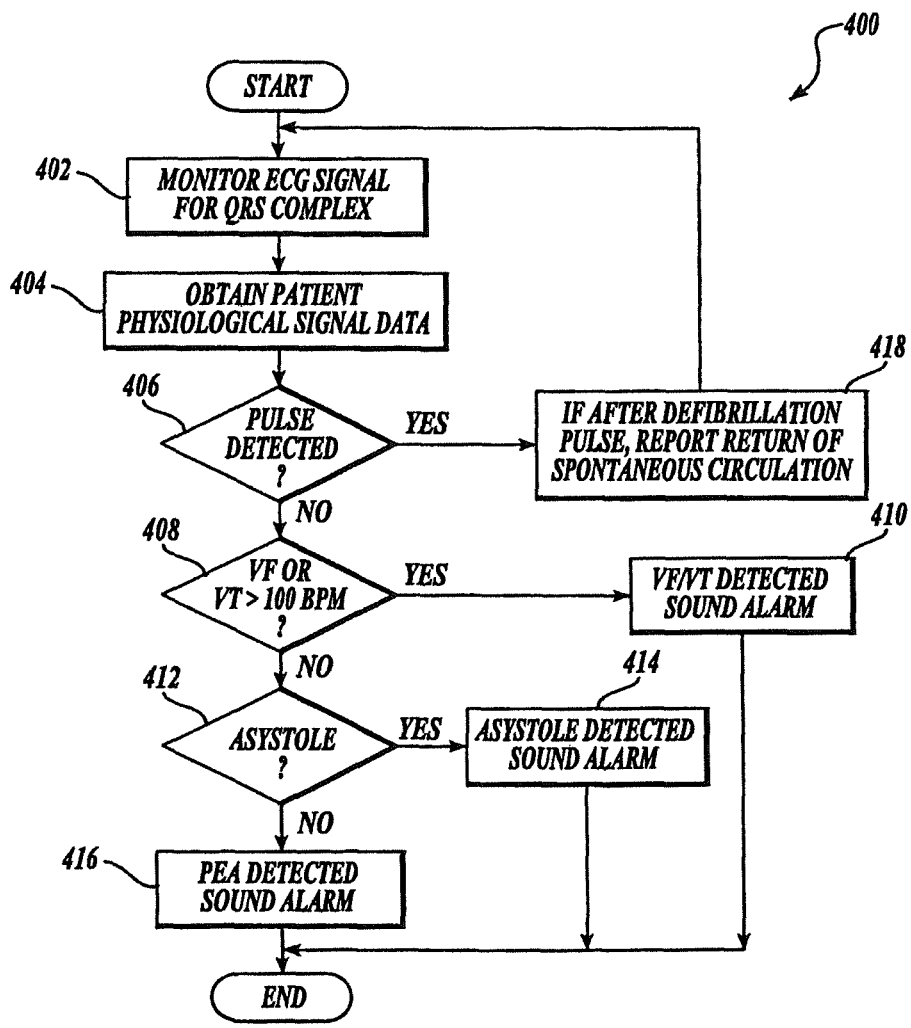
FIG. 19 is a flow diagram of a patient condition advisory process for use in a medical device that incorporates a pulse detection process of the present invention.

FIG. 19 illustrates still another application in which pulse detection according to the present invention may be used. The process 400 described in FIG. 19 is particularly suited for use in a manual defibrillator or patient monitor. Beginning at block 402, the process 400 monitors the patient's ECG for QRS complexes. At block 404, the process 400 also obtains other physiological signal data, such as PCG data, impedance signal data, piezoelectric signal data, accelerometer data, etc., from the patient. The process 400 uses the ECG and other physiological signal data in decision block 406 to determine the presence of a cardiac pulse. The pulse detection implemented in block 406 may be one of the pulse detection processes discussed herein.

If a pulse is detected, the process 400 determines whether a defibrillation pulse has been provided to the patient and if so, reports the return of spontaneous circulation to the operator, as indicated at block 418. The process 400 then returns to block 402 to repeat the pulse detection analysis. If a pulse is not detected, the process 400 evaluates the ECG signal to determine whether the patient is experiencing ventricular fibrillation or ventricular tachycardia with a heart rate greater than 100 bpm. If so, then the process identifies the patient's condition and produces a VT/VF alarm, as indicated at block 410. If not, the process 400 then proceeds to block 412 to check for an asystole condition.

Detection of asystole may be accomplished as noted earlier and described in greater detail in U.S. Pat. No. 6,304,773, incorporated herein by reference. If asystole is detected, the process 400 identifies the patient's condition and sounds an asystole alarm, as indicated at block 414. Otherwise, the patient is experiencing PEA and the patient's condition is so identified, with the sound of a PEA alarm, as indicated at block 416. In this manner, the operator of the manual defibrillator or monitor is kept advised of the patient's condition.

One having ordinary skill in the art will readily recognize that the present invention may be implemented by one or more devices that include logic circuitry. The one or more devices perform functions and/or methods as described above. The logic circuitry may include a processor, such as the processing circuit 38, that may be programmable for a general purpose, or dedicated, such as a microcontroller, a microprocessor, a digital signal processor (DSP), etc. For example, a device implementing the invention may be a digital computer-like device, such as a general purpose computer selectively activated or reconfigured by a computer program stored in the computer. Alternatively, the device may be implemented as an application specific integrated circuit (ASIC), etc.

The invention additionally provides methods and algorithms as described above. The methods and algorithms presented above are not necessarily inherently associated with any particular computing device or other apparatus. Rather, various general purpose machines may be used with programs in accordance with the teachings herein, or it may prove more convenient to construct more specialized apparatus to perform the required method steps. The required structure for a variety of these machines is apparent from the description herein.

In all cases, it should be borne in mind the distinction between the method of the invention itself and the method of operating a computing machine. The present invention relates to both methods in general, and also to steps for operating a computer and for processing electrical or other physical signals to generate other desired physical signals.

The invention additionally provides programs and methods of program operation. A program is generally defined as a group of steps leading to a desired result. A program made according to an embodiment of the invention is most advantageously implemented as a program for a computing machine, such as a defibrillator 10 or other equipment housing a general purpose computer, a special purpose computer, a microprocessor, etc.

The invention also provides storage media that, individually or in combination with others, have stored thereon instructions of a program made according to the invention. A storage medium according to the invention is a computer-readable medium, such as a memory 40 as noted above, and is read by the computing machine mentioned above.

It is readily apparent that the steps or instructions of a program made according to an embodiment of the invention requires physical manipulations of physical quantities. Usually, though not necessarily, these quantities may be transferred, combined, compared, and otherwise manipulated or processed according to the instructions, and they may also be stored in a computer-readable medium. These quantities include, for example, electrical, magnetic, and electromagnetic signals, and also states of matter that can be queried by such signals. It is convenient at times, principally for reasons of common usage, to refer to these quantities as signal data, bits, data bits, samples, values, symbols, characters, images, terms, numbers, or the like. It should be borne in mind, however, that all these and similar terms are associated with the appropriate physical quantities, that these terms are merely convenient labels applied to these physical quantities.

This detailed description is presented largely in terms of flowcharts, display images, algorithms, processes, and symbolic representations of operations of data bits within at least one computer readable medium. The present description achieves an economy in that a single set of flowcharts is used to describe both methods of the invention and programs according to the invention. Such descriptions and representations are the type of convenient labels used by those skilled in programming and/or data processing arts to effectively convey the substance of their work to others skilled in the art. A person skilled in the art of programming may use these descriptions to readily generate specific instructions for implementing a program according to the present invention.

Often, and for the sake of convenience only, it is preferred to implement and describe a program as various interconnected distinct software modules or features, individually and collectively also known as software, though such modules may equivalently be aggregated into a single program with unclear boundaries. The software modules or features of the present invention may be implemented by themselves, or in combination with others. Although the program may be stored in a computer-readable medium, such as a memory 40, a person skilled in the art will readily recognize that it need not be a single memory, or even a single machine. Various portions, modules, or features of the program may reside in separate memories, or even separate machines. The separate machines may be connected directly, or through a network, such as a local area network (LAN), or a global network, such as the Internet, by wired or wireless connections. For example, a data acquisition unit may collect the accelerometer signal data obtained in the present invention and communicate the data to a remote computing machine for analysis and report whether a cardiac pulse is present.

It will be appreciated that some of the methods described herein may include software steps that can be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is performed in which plane.

In any event, in the present case, methods of the invention are implemented by machine operations. In other words, embodiments of programs of the invention are made such that they perform methods of the invention as described above. These may optionally be performed in conjunction with one or more human operators performing some, but not all of them. As per the above, these need not be co-located with each other, but each only with a machine that houses a portion of the program. Alternatively, some of these machines may operate automatically, without users and/or independently from each other and/or may be wearable by the user or may be attached to the user.

While various exemplary embodiments of the invention have been illustrated and described herein, persons having ordinary skill in the art will recognize variations of the same that are fully with the scope of the invention. Embodiments of the invention described herein are shown processing digital physiological signal data. However, the invention also includes embodiments in which the physiological signal data is not converted to digital form, but remains in analog form. References to "data" thus encompass both digital and analog signal formats. Moreover, references to "physiological signal data" may refer to a raw physiological signal itself or signal information derived from the physiological signal in either digital or analog form.

The invention claimed is:

1. A device for providing treatment to a patient, comprising:
    a pulse sensor configured to sense a pulse of the patient and output patient pulse data;
    a breathing detection element configured to detect whether the patient is breathing and to output patient breathing data;
    a controller operatively coupled to the pulse sensor and the breathing detection element and structured to
    analyze the output patient pulse data;
    determine that the patient has a pulse based on the analyzed output patient pulse data;
    analyze the output patient breathing data;
    determine that the patient is not breathing based on the analyzed output patient pulse data; and
    generate an instruction to provide rescue breathing to the patient based on the determination that the patient has a pulse and the determination that the patient is not breathing; and
    an output device configured to issue a prompt to provide rescue breathing to the patient based on the generated instruction.

2. The device of claim 1, wherein the pulse sensor comprises a phonocardiogram (PCG) electrode configured to sense PCG signals in the patient.

3. The device of claim 1, wherein the pulse sensor comprises a light source and a photodetector.

4. The device of claim 1, further comprising a motion detection device structured to detect a motion of the patient, wherein the motion detection device is coupled to the controller.

5. The device of claim 4, wherein the motion detection device includes a patient impedance measuring device to measure a patient impedance.

6. The device of claim 4, wherein the motion detection device is configured to transmit a motion detection input to the controller, and wherein, when motion is detected by the motion detection device and indicated in the motion detection input, the controller is further configured to generate the instruction based on the motion detection input and the instruction includes an instruction not to deliver a defibrillation shock to the patient, the instruction based, at least in part, on the detected motion in the motion detection input.

7. The device of claim 6, wherein the output device is further configured to issue a prompt to reduce motion when the motion detection device detects that there is a motion.

8. The device of claim 1, wherein the device comprises a cardiac monitor.

9. The device of claim 8, wherein the cardiac monitor is configured to be electrically coupled to a defibrillator that is positioned remote from the cardiac monitor, and wherein the controller is structured to transmit data that indicates the instruction to the defibrillator.

10. The device of claim 1, wherein the device is configured to be electrically coupled to a defibrillator that is positioned remote from the device, and wherein the controller is structured to transmit data that indicates the instruction to the defibrillator.

11. A method for providing treatment to a patient, comprising:
    sensing by a pulse sensor a pulse of the patient;
    generating output patient pulse data based on the sensed pulse;
    detecting by one or more sensors whether the patient is breathing;
    generating output patient breathing data based on the detected patient breathing;
    analyzing the output patient pulse data and determining that the patient has a pulse based on the analyzed output patient pulse data;
    analyzing the output patient breathing data and determining that the patient is not breathing based on the analyzed output patient breathing data;
    prompting a caregiver to provide rescue breathing based on the output patient pulse data that the patient has a pulse and the output patient breathing data that the patient is not breathing.

12. The method of claim 11, further comprising:
    determining whether the patient is moving; and
    performing one or both of sending an instruction or generating a prompt to inhibit defibrillation and prompting a caregiver to reduce motion when the patient is determined to be moving.

13. The method of claim 12, wherein determining whether the patient is moving comprises measuring a patient impedance.

14. The method of claim 11, wherein detecting whether the patient is breathing comprises:
    determining a rescue breathing protocol based on the output patient pulse data and the output patient breathing data.

15. The method of claim 11, further comprising transmitting data including the output patient pulse data and the output patient breathing data to a defibrillator, the defibrillator configured to apply defibrillation therapy to the patient based on the output patient pulse data and the output patient breathing data.

16. The method of claim 15, wherein the pulse sensor and the one or more sensors that detect whether the patient is breathing are included in a medical device.

17. The method of claim 16, wherein the medical device is a cardiac monitor.

18. The method of claim 16, wherein the medical device is remote from the defibrillator.

19. A device for providing treatment to a patient, comprising:

a pulse sensor configured to sense a pulse of the patient and output patient pulse data;

one or more sensors configured to detect breathing in the patient and to output patient breathing data indicative of whether the patient is breathing;

a controller operatively coupled to the pulse sensor and the one or more sensors configured to detect breathing in the patient, the controller configured to receive the output patient pulse data and the output patient breathing data and structured to analyze the output patient pulse data;

determine that the patient has a pulse based on the analyzed output patient pulse data;

analyze the output patient breathing data;

determine that the patient is not breathing based on the analyzed output patient pulse data; and generate an instruction to provide rescue breathing to the patient based on the determination that the patient has a pulse and the determination that the patient is not breathing; and an output device configured to issue a prompt to provide rescue breathing to the patient if the output patient pulse data indicates that the patient has a pulse and the the output patient breathing data indicates that the patient is not breathing.

* * * * *

UNITED STATES PATENT AND TRADEMARK OFFICE
CERTIFICATE OF CORRECTION

PATENT NO. : 9,248,306 B2
APPLICATION NO. : 13/970522
DATED : February 2, 2016
INVENTOR(S) : Tae H. Joo et al.

It is certified that error appears in the above-identified patent and that said Letters Patent is hereby corrected as shown below:

On the title page,

Under item (60), Related U.S. Application Data, line 5, page 2, replace "filed September 3, 1999" with -- September 30, 1999 --.

In the specification,

After line 26, column 3, insert the following paragraph:

-- A feature indicating the presence of a pulse may be obtained from an evaluation of temporal parameters or spectral parameters in the physiological signal data. In one aspect, temporal energy may be evaluated by estimating instantaneous and background energies in the signal data and comparing the instantaneous energy with the background energy. Energy in the signal data may also be calculated and compared with a threshold energy. In another aspect, spectral energy may be evaluated by locating a peak energy value in the energy spectrum and comparing the peak energy value with a threshold energy value. Alternatively, or in addition, the frequency of the peak energy value in the spectrum may be compared with a threshold frequency. --.

Signed and Sealed this
Nineteenth Day of July, 2016

Michelle K. Lee
*Director of the United States Patent and Trademark Office*